US007615635B2

(12) United States Patent
Bracken et al.

(10) Patent No.: US 7,615,635 B2
(45) Date of Patent: Nov. 10, 2009

(54) N-FORMYL HYDROXYLAMINES

(75) Inventors: Kathryn Rene Bracken, Swampscott, MA (US); Simon Bushell, Boston, MA (US); Karl Dean, Marlborough, MA (US); Charles Francavilla, Fremont, CA (US); Rakesh K. Jain, Fremont, CA (US); Kwangho Lee, Lexington, MA (US); Mohindra Seepersaud, Belmont, MA (US); Lei Shu, Woburn, MA (US); Arathi Sundaram, Fremont, CA (US); Zhengyu Yuan, Palo Alto, CA (US)

(73) Assignees: Novartis AG, Basel (CH); Vicuron Pharmaceuticals, Inc., Vienna (AT)

( * ) Notice: Subject to any disclaimer, the term of this patent is extended or adjusted under 35 U.S.C. 154(b) by 80 days.

(21) Appl. No.: 11/914,659

(22) PCT Filed: May 22, 2006

(86) PCT No.: PCT/US2006/019688

§ 371 (c)(1), (2), (4) Date: Nov. 16, 2007

(87) PCT Pub. No.: WO2006/127576

PCT Pub. Date: Nov. 30, 2006

(65) Prior Publication Data

US 2008/0161558 A1 Jul. 3, 2008

Related U.S. Application Data

(60) Provisional application No. 60/683,655, filed on May 23, 2005.

(51) Int. Cl.
| | |
|---|---|
| C07D 403/12 | (2006.01) |
| A61K 31/501 | (2006.01) |
| A61K 31/497 | (2006.01) |
| A61K 31/506 | (2006.01) |
| A61K 31/4439 | (2006.01) |
| C07D 401/12 | (2006.01) |
| C07D 309/10 | (2006.01) |
| C07D 207/08 | (2006.01) |
| A61P 31/04 | (2006.01) |

(52) U.S. Cl. ............. 544/336; 544/224; 544/329; 544/408; 544/409; 546/279.1; 549/419; 548/230; 548/532

(58) Field of Classification Search ............. 544/336
See application file for complete search history.

(56) References Cited

U.S. PATENT DOCUMENTS

| 6,797,820 B2 | 9/2004 | Patel et al. |
|---|---|---|
| 6,852,752 B2 | 2/2005 | Jacobs et al. |
| 6,987,104 B2 | 1/2006 | Jacobs et al. |
| 7,148,242 B2 | 12/2006 | Jacobs et al. |
| 7,452,999 B2 | 11/2008 | Prashad et al. |
| 2005/0261504 A1 | 11/2005 | Kapa et al. |
| 2005/0277683 A1 | 12/2005 | Jacobs et al. |
| 2007/0060753 A1 | 3/2007 | Slade et al. |
| 2007/0135353 A1 | 6/2007 | Slade et al. |

FOREIGN PATENT DOCUMENTS

| WO | WO-02/102790 A1 | 12/2002 |
|---|---|---|

OTHER PUBLICATIONS

Fritsche, Thomas R. et al., "Comparative Antimicrobial Characterization of LBM415 (NVP PDF-713), a New Peptide Deformylase Inhibitor of Clinical Importance," *Antimicrobial Agents and Chemotherapy*, vol. 49(4):1468-1476 (2005).

*Primary Examiner*—Mark L Berch
*Assistant Examiner*—Cecilia M Jaisle
(74) *Attorney, Agent, or Firm*—McCarter & English, LLP; Elizabeth A. Hanley, Esq.; Joshua K. Roth

(57) ABSTRACT

Novel N-formyl hydroxylamine compounds and their derivatives are disclosed. These N-formyl hydroxylamine compounds inhibit peptidyl deformylase (PDF), an enzyme present in prokaryotes. The compounds are useful as antimicrobials and antibiotics. The compounds of the invention display selective inhibition of peptidyl deformylase versus other metalloproteinases such as MMPs. Methods of preparation and use of the compounds are also disclosed.

13 Claims, No Drawings

N-FORMYL HYDROXYLAMINES

This application is a US National Phase filing of PCT/US2006/019688 filed May 22, 2006, which claims priority to U.S. Provisional Application 60/683,655 filed May 23, 2005.

This invention is directed to novel N-formyl hydroxylamine compounds, to the uses of these compounds in various medicinal applications, including treating disorders amenable to treatment by peptidyl deformylase inhibitors such as treatment of bacterial infections, and to pharmaceutical compositions comprising these compounds.

Treatment of microbial infection in host organisms requires an effective means to kill the microbe while doing as little harm to the host as possible. Accordingly, agents which target characteristics unique to a pathology-causing microorganism are desirable for treatment.

Peptide deformylase is a metallopeptidase found in prokaryotic organisms such as bacteria. Protein synthesis in prokaryotic organisms begins with N-formyl methionine (fMet). After initiation of protein synthesis, the formyl group is removed by the enzyme peptide deformylase (PDF); this activity is essential for maturation of proteins.

Metalloproteinases are critical to many aspects of normal metabolism. Disorders involving metalloproteinases have been implicated in several diseases such as cancer, arthritis, and autoimmune diseases. Because of the importance of MMPs in normal physiological processes, it would be preferable to develop agents that inhibit PDF while avoiding significant inhibition of MMPs. Alternatively, PDF inhibitors which also inhibit MMPs may be of use where the therapeutic benefits of inhibiting PDF outweigh the risk of side effects from MMP inhibition.

Research on inhibitors of PDF is much less extensive than that for inhibitors of MMPs. N-formyl hydroxylamine derivatives are described in International Patent Application WO 99/39704 and WO 02/102790. In view of the importance of identifying new antibiotics to treat bacteria resistant to existing antibiotics, it is desirable to develop novel inhibitors of PDF for evaluation and use as antibacterial and antimicrobial agents. The present invention fulfills this need.

In particular, the present invention provides an N-formyl hydroxylamine derivatives referred to herein collectively as "compounds of the invention"), a salt thereof or a prodrug thereof, e.g. a compound of formula (I):

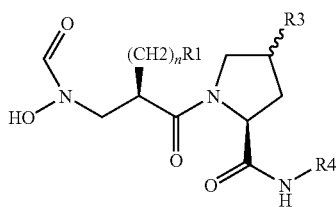

wherein $R_1$ is hydrogen, alkyl, heteroalkyl, heterocycloalkyl, aryl or heteroaryl;

$R_3$ is hydrogen, halogen, or alkoxy; and $R_4$ is aryl, or heteroaryl; or n is 0 to 3 a salt thereof or a prodrug thereof.

In one aspect, $R_4$ is a heteroaryl of formula (II)

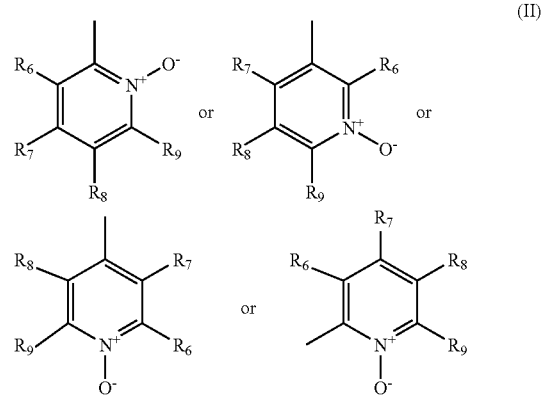

wherein each of $R_6$, $R_7$, $R_8$ and $R_9$ independently is hydrogen, alkyl, substituted alkyl, phenyl, halogen, hydroxy or alkoxy, e.g. wherein a.) $R_6$ and $R_8$ are hydrogen, $R_9$ is hydrogen or alkyl and $R_7$ is alkyl, substituted alkyl or phenyl;

b.) $R_6$, $R_7$ and $R_9$ are hydrogen and $R_8$ is halogen, alkyl or substituted alkyl c.) $R_7$, $R_8$ and $R_9$ are hydrogen and $R_6$ is hydroxyl.

In a particularly useful aspect, the heteroaryl is of the formula (II.1)

wherein $R_6$, $R_7$ and $R_9$ are as defined above for formula (II) and $R_8$ is halogen, e.g. fluoro.

In yet another aspect, $R_4$ is of formula (II.2)

wherein $R_6$, $R_7$ and $R_8$ are as defined above for formula (II) above

In still another aspect, $R_4$ is of formula (II.3)

wherein $R_6$, $R_7$ and $R_8$ are as defined above for formula (II)

In still another aspect, $R_4$ is of formula (II.4)

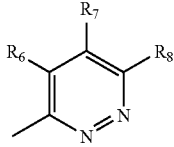

(II.4)

wherein $R_6$, $R_7$ and $R_8$ are as defined above for formula (II)

In still another aspect, R4 is of formula (II.5)

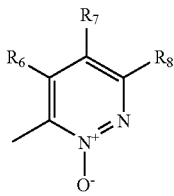

(II.5)

wherein $R_6$, $R_7$ and $R_8$ are as defined above for formula (II)

Unless otherwise stated, the following terms as used in the specification have the following meaning.

The term "cycloalkane" or cycloalkyl" contains from 3- to 7-ring carbon atoms, and is, preferably cyclopropyl, cyclobutyl, cyclopentyl, and cyclohexyl.

The term "aliphatic group" refers to saturated or unsaturated aliphatic groups, such as alkyl, alkenyl or alkynyl, cycloalkyl or substituted alkyl including straight-chain, branched-chain and cyclic groups having from 1-10 carbons atoms. The term "alkyl" or "alk", whenever it occurs, is a saturated straight chain or branched aliphatic group of 1-10 carbon atoms or a cycloalkyl of 3-10 carbon atoms, more preferably, alkyl groups are $C_1$-$C_7$alkyl, particularly, $C_1$-$C_4$alkyl. Examples of "alkyl" or "alk" include, but are not limited to, methyl, ethyl, n-propyl, isopropyl, n-butyl, isobutyl, sec-butyl, t-butyl, n-pentyl, neopentyl, n-hexyl or n-heptyl, cyclopropyl and, especially, n-butyl.

The term "substituted alkyl" refers to an alkyl group that is substituted with one or more substitutents preferably 1 to 3 substitutents including, but not limited to substituents such as halogen, lower alkoxy, hydroxy, mercapto, carboxy, cycloalkyl, aryl, heteroaryl, and the like. Examples of substituted alkyl groups include, but are not limited to, —$CF_3$, —$CF_2$—$CF_3$, hydroxymethyl, 1- or 2-hydroxyethyl, methoxymethyl, 1- or 2-ethoxyethyl, carboxymethyl, 1- or 2-carboxyethyl, and the like.

The term "aryl" or "Ar" refers to an aromatic carbocyclic group of 6 to 14 carbon atoms having a single ring (including, but not limited to, groups such as phenyl) or multiple condensed rings (including, but not limited to, groups such as naphthyl or anthryl), and is especially phenyl.

The term "heteroaryl" or "HetAr" refers to a 4- to 7-membered, monocyclic aromatic heterocycle or a bicycle that is composed of a 4- to 7-membered, monocyclic aromatic heterocycle and a fused-on benzene ring. The heteroaryl has at least one hetero atom, preferably at least two heteroatoms including, but not limited to, heteroatoms such as N, O and S, within the ring. A preferred heteroaryl moiety is a 6 membered, monocyclic heterocycle having 2, 3 or 4 nitrogen heteroatoms in the ring. Examples of heteteroaryl groups are pyridinyl, pyrimidinyl, pyrazinyl, pyridazinyl, pyridazinyl N-oxide or benzdioxolanyl, triazine or tetrazines.

The aryl or heteroaryl may be unsubstituted or substituted by one or more substituents including, but not limited to $C_{1-7}$ alkyl, particularly $C_{1-4}$ alkyl such as methyl, hydroxy, alkoxy, acyl, acyloxy, SCN, cyano, nitro, thioalkoxy, phenyl, heteroalkylaryl, alkylsulfonyl, halogen, and formyl.

The term "heteroalkyl" refers to saturated or unsaturated $C_{1-8}$ alkyl as defined above, and especially $C_{1-4}$ heteroalkyl which contain one or more heteroatoms, as part of the main, branched, or cyclic chains in the group. Heteroatoms may independently be selected from the group consisting of —NR— where R is hydrogen or alkyl, —S—, —O—, and —P—; preferably —NR— where R is hydrogen or alkyl, and/or —O—. Heteroalkyl groups may be attached to the remainder of the molecule either at a heteroatom (if a valence is available) or at a carbon atom. Examples of heteroalkyl groups include, but are not limited to, groups such as —O—$CH_3$, —$CH_2$—O—$CH_3$, —$CH_2$—$CH_2$—O—$CH_3$, —S—$CH_2$—$CH_2$—$CH_3$, —$CH_2$—$CH(CH_3)$—S—$CH_3$, and —$CH_2$—$CH_2$—NH—$CH_2$—$CH_2$—.

The heteroalkyl group may be unsubstituted or substituted with one or more substituents, preferably one to three substituents, including but not limited to, alkyl, halogen, alkoxy, hydroxyl, mercapto, carboxy, and especially phenyl. The heteroatom(s) as well as the carbon atoms of the group may be substituted. The heteroatom(s) may also be in oxidized form.

The term "alkoxy" as used herein refers to a $C_{1-10}$ alkyl linked to an oxygen atom, or preferably $C_{1-7}$ alkoxy, more preferably $C_{1-4}$ alkoxy. Examples of alkoxy groups include, but are not limited to, groups such as methoxy, ethoxy, n-butoxy, tert-butoxy, and allyloxy.

The term "halogen" or "halo" as used herein refer to chlorine, bromine, fluorine, iodine, and is especially fluorine.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups may be found in Greene et al., "Protective Groups in Organic Synthesis", 2nd Ed., John Wiley & Sons, Inc., New York (1991). Preferred amino protecting groups include, but are not limited to, benzyloxycarbonyl (CBz), t-butyl-oxycarbonyl (Boc), t-butyldimethylsilyl (TBDMS),9-fluorenylmethyl-oxycarbonyl (Fmoc), or suitable photolabile protecting groups such as 6-nitroveratryloxy carbonyl (Nvoc), nitropiperonyl, pyrenylmethoxycarbonyl, nitrobenzyl, dimethyl dimethoxybenzyl, 5-bromo-7-nitroindolinyl, and the like. Preferred hydroxy protecting groups include Fmoc, TBDMS, photolabile protecting groups (such as nitroveratryl oxymethyl ether (Nvom)), Mom (methoxy methyl ether), and Mem (methoxy ethoxy methyl ether). Particularly preferred protecting groups include NPEOC (4-nitrophenethyloxycarbonyl) and NPEOM (4-nitrophenethyloxy-methyloxycarbonyl).

It will be appreciated that the compounds of formula (I) may exist in the form of optical isomers, racemates or diastereoisomers. For example, a compound of formula (I) wherein R3 may be in the R- or S-configuration. It is to be understood that the present invention embraces all enantiomers and their mixtures. Similar considerations apply in relation to starting materials exhibiting asymmetric carbon atoms as mentioned.

The compounds of the invention may exist in the form of solid crystalline salts. Preferably the crystalline salts are metal salts, preferably of divalent metals, although for some compounds it is possible to form crystalline solids by using monovalent counter ions, such as Na. The counter ion is preferably Mg, Ca or Zn.

The compounds of the invention may typically be in the form of a hydrate or a mixed solvate/hydrate. Typically, the crystalline salt of the invention contains about 2 to 8 waters of hydration, more typically about 2 to 6 waters of hydration, and even more typically about 2 to 4 waters of hydration. Thus, the crystalline salt of the invention typically comprises greater than 2% water, more typically about 4 to about 12% water and even more typically about 8 to about 9% water. Solvates may be of one or more organic solvents, such as lower alkyl alcohols, such as methanol, ethanol, isopropanol, butanol or mixtures thereof.

The compounds of the invention, e.g. the compounds of formula (I), may exist in free form or in salt form, e.g. in form of a pharmaceutically acceptable salt. A "pharmaceutically acceptable salt" of a compound means a physiologically and pharmaceutically acceptable salt that possesses the desired pharmacological activity of the parent compound and does not impart undesired toxicological effects. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, tromethamine, N-methylglucamine, and the like.

A compound of the invention, e.g. the compounds of formula (I), may act as a pro-drug. "Prodrug" means any compound which releases an active parent drug according to formula (I) in vivo when such prodrug is administered to a mammalian subject. Prodrugs of a compound of formula (I) are prepared by modifying functional groups present in the compound of formula (I) in such a way that the modifications may be cleaved in vivo to release the parent compound. Prodrugs include compounds of formula (I) wherein a hydroxy, amino, or sulfhydryl group is bonded to any group that may be cleaved in vivo to regenerate the free hydroxyl, amino, or sulfhydryl group, respectively. Examples of prodrugs include, but are not limited to esters (e.g. acetate, formate, and benzoate derivatives), carbamates (e.g. N,N-dimethylaminocarbonyl) of hydroxy functional groups in compounds of formula (I), and the like.

In the compounds of formula (I), the following significances are preferred individually or in any sub-combination:

1. $R_4$ is a heteroaryl of formula of (II.1) wherein $R_6$, $R_7$ and $R_9$ are hydrogen and $R_8$ is fluoro, $R_6$, $R_7$ and $R_9$ are hydrogen and $R_8$ is methyl or trifluoromethyl; or $R_6$, $R_7$ and $R_8$ are hydrogen and $R_9$ is fluoro; or $R_6$, $R_8$ and $R_9$ are hydrogen and $R_7$ is ethyl or methoxy; or $R_7$, $R_8$ and $R_9$ are hydrogen and $R_6$ is hydroxy; or $R_7$ and $R_8$ are hydrogen, $R_6$ is methoxy and $R_9$ is methyl; or R4 is a heteroaryl of formula (II.2) wherein $R_6$, $R_7$ and $R_8$ are hydrogen, or R4 is a heteroaryl of formula (II.3) wherein R6, R7 and R8 are hydrogen, or R4 is a heteroaryl of formula (II.4) wherein R6, R7 and R8 are hydrogen or R4 is a heteroaryl of formula (II.5) wherein R6, R7 and R8 are hydrogen.

2. R1 is alkyl, preferably n-butyl or cycloalkyl, preferably $C_{3-7}$ cycloalkyl such as cyclohexyl, cyclopropyl, or cyclopentyl 4. R3 is halogen, preferably fluoro;

Utility

The compounds of the present invention can be used for the treatment or prevention of infectious disorders caused by a variety of bacterial or prokaryotic organisms. Examples include, but are not limited to, Gram positive and Gram negative aerobic and anaerobic bacteria, including Staphylococci, e.g., *S. aureus* and *S. epidermidis*; Enterococci, e.g., *E. faecalis* and *E. faecium*; Streptococci, e.g., *S. pneumoniae; Haemophilus*, e.g., *H. influenza; Moraxella*, e.g., *M. catarrhalis*; and *Escherichia*, e.g., *E. coli*. Other examples include *Mycobacteria*, e.g., *M. tuberculosis*; intercellular microbes, e.g., *Chlamydia* and *Rickettsiae*; and *Mycoplasma*, e.g., *M. pneumoniae*; and *Pseudomonas*, e.g., *P. aeruginosa; H. pylori*; and parasites, e.g., *Plasmodium falciparum*.

Compounds of the present invention preferably have substantial improvement in microbiological efficacy against either Gram positive or Gram negative bacteria. Specifically, the compounds of the present invention have significant improvement in their microbiological spectrum of activity by having improved inhibition of Gram negative and/or Gram positive bacteria such as *H. influenza* and *S pneumonia*. For example where, in one example, the average comparative index (ACI) is greater than 3 dilution steps for the improved inhibition of *H. influenza* and additionally shows an ACI of 0.4 dilution steps for the improved inhibition of *S. pneumonia*. In another example, the ACI is 3 dilution steps for the improved inhibition of *S. pneumonia* and additionally shows an ACI of 1.2 dilution steps for the improved inhibition of *H. influenza*.

The compounds of the invention also preferably have improved safety, toxicity and pharmacokinetic properties, e.g. a decrease or elimination of potential adverse events in human relative to prior art compounds.

In one aspect, compositions, for treating or preventing infectious disorders are provided, comprising a compound of the invention, a pharmaceutically acceptable salt thereof or a prodrug thereof, as disclosed herein in combination with a pharmaceutically acceptable carrier. In another embodiment, such compositions further include another therapeutic agent.

In another aspect, there is provided a dosage amount of a compound of the invention, a pharmaceutically acceptable salt thereof or a prodrug thereof, as disclosed herein in an effective amount for the treatment, prevention or alleviation of a disorder, such as an infectious disorder. These compounds or derivatives thereof can be screened for activity against different microbial agents and appropriate dosages can be determined using methods available in the art.

The compounds of the invention can be used to treat a subject to treat, prevent, or reduce the severity of an infection. Subjects include animals, plants, blood products, cultures and surfaces such as those of medical or research equipment, such as glass, needles, surgical equipment and tubing, and objects intended for temporary or permanent implantation into an organism. Preferred animals include mammals, e.g., mice, rats, cats, dogs, cows, sheep, pigs, horses, swine, primates, such as rhesus monkeys, chimpanzees, gorillas, and most preferably humans. Treating a subject includes, but is not limited to, preventing, reducing, or eliminating the clinical symptoms caused by an infection of a subject by a microorganism; preventing, reducing, or eliminating an infection of a subject by a microorganism; or preventing, reducing, or eliminating contamination of a subject by a microorganism. The microorganism involved is preferably a prokaryote, more preferably a bacterium.

In one aspect, methods of treating or preventing an infectious disorder in a subject, such as a human or other animal subject, that are responsive to inhibition of peptidyl deformylase are provided, by administering to the subject an effective peptidyl deformylase inhibiting amount of a compound of the invention, a pharmaceutically acceptable salt thereof or a prodrug thereof. In one embodiment, the compound or its derivative is administered in a pharmaceutically acceptable form optionally in a pharmaceutically acceptable carrier. The compound of the invention, pharmaceutically acceptable salt thereof or prodrug thereof, can be administered alone or in combination with another therapeutic agent. Examples of such therapeutic agents include, but are not limited to, β-lactam, quinolone, macrolide, glycopeptide and oxazolidinone. As used herein, an "infectious disorder" is any disorder characterized by the presence of a microbial infection, such as the presence of bacteria. Such infectious disorders include, for example, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, antibacterial prophylaxis in immunosuppressed patients, such as patients receiving cancer chemotherapy, or organ transplant patients and chronic diseases caused by infectious organisms, e.g., arteriosclerosis. The compounds and compositions comprising the compounds can be administered by routes such as topically, locally or systemically. Systemic application includes any method of introducing the compound into the tissues of the body, e.g., intrathecal, epidural, intramuscular, transdermal, intravenous, intraperitoneal, subcutaneous, sublingual, nasal, vaginal, rectal, and oral administration. The specific dosage of antimicrobial to be administered, as well as the duration of treatment, can be adjusted as needed.

In another aspect of the present invention, methods are provided for inhibiting peptidyl deformylase. In one embodiment, the method comprises administering to a subject in need thereof an effective peptidyl deformylase inhibiting amount of a compound of formula (I), a pharmaceutically acceptable salt thereof or a prodrug thereof. The terms "subject" and "effective peptidyl deformylase inhibiting amount" are as defined above.

In yet another aspect of the invention, there is also provided the use of a compound of the formula (I) as defined above, a pharmaceutically acceptable salt thereof or a prodrug thereof in the preparation of a medicament for use in the treatment of diseases mediated by peptidyl deformylase.

Administration and Pharmaceutical Composition

The present invention also provides pharmaceutical compositions which comprise a bioactive N-formyl hydroxylamine compound, a pharmaceutically acceptable salt thereof, or a prodrug thereof and a pharmaceutically acceptable carrier. The compositions of the invention include those in a form adapted for oral, topical or parenteral use and can be used for the treatment of bacterial infection in a subject such as animals, preferably, mammals, more preferably, humans. The pharmaceutical compositions can further include another therapeutic agent as described below.

The antibiotic compounds, also referred to herein as antimicrobial compounds, according to the invention can be formulated for administration in any convenient way for use in human or veterinary medicine, by analogy with other antibiotics. Such methods are known in the art (see, e.g., Remington's Pharmaceutical Sciences, Easton, Pa.: Mack Publishing Co.) and are not described in detail herein.

The composition can be formulated for administration by any route known in the art, such as subdermal, inhalation, oral, topical or parenteral. The compositions can be in any form known in the art, including but not limited to tablets, capsules, wafers, fast melts (without wafers), powders, granules, lozenges, creams or liquid preparations, such as oral or sterile parenteral solutions or suspensions. The compounds can also be administered in liposomal, micellar or microemulsion formulations. The compounds can also be administered as prodrugs, where the prodrug administered undergoes biotransformation in the treated mammal to a form which is biologically active.

The topical formulations of the present invention can be presented as, for instance, ointments, creams or lotions, solutions, salves, emulsions, plasters, eye ointments and eye or ear drops, impregnated dressings, transdermal patches, sprays and aerosols, and can contain appropriate conventional additives such as preservatives, solvents to assist drug penetration and emollients in ointments and creams.

The formulations can also contain compatible conventional carriers, such as cream or ointment bases and ethanol or oleyl alcohol for lotions. Such carriers can be present, for example, from about 1% up to about 99% of the formulation. For example, they can form up to about 80% of the formulation.

Tablets and capsules for oral administration can be in unit dose presentation form, and can contain conventional excipients such as binding agents, for example, syrup, acacia, gelatin, sorbitol, tragacanth, or polyvinylpyrollidone; fillers, for example, lactose, sugar, maize-starch, calcium phosphate, sorbitol or glycine; tabletting lubricants, for example, magnesium stearate, talc, polyethylene glycol or silica; disintegrants, for example, potato starch; or acceptable wetting agents, such as sodium lauryl sulphate. The tablets can be coated according to methods well-known in standard pharmaceutical practice.

Oral liquid preparations can be in the form of, for example, aqueous or oily suspensions, solutions, emulsions, syrups or elixirs, or can be presented as a dry product for reconstitution with water or another suitable vehicle before use. Such liquid preparations can contain conventional additives, such as suspending agents, for example, sorbitol, methyl cellulose, glucose syrup, gelatin, hydroxyethyl cellulose, carboxymethyl cellulose, aluminium stearate gel or hydrogenated edible fats; emulsifying agents, for example, lecithin, sorbitan monooleate, or acacia; non-aqueous vehicles (which can include edible oils), for example, almond oil, oily esters such as glycerine, propylene glycol, or ethyl alcohol; preservatives, for example, methyl or propyl p-hydroxybenzoate or sorbic acid, and, if desired, conventional flavoring or coloring agents.

For parenteral administration, fluid unit dosage forms are prepared utilizing the compound and a sterile vehicle, water being preferred. The compound, depending on the vehicle and concentration used, can be either suspended or dissolved in the vehicle or other suitable solvent. In preparing solutions, the compound can be dissolved in water for injection and filter sterilized before filling into a suitable vial or ampule and sealing. Advantageously, agents such as a local anesthetic preservative and buffering agents can be dissolved in the vehicle. To enhance the stability, the composition can be frozen after filling into the vial and the water removed under vacuum. The dry lyophilized powder is then sealed in the vial and an accompanying vial of water for injection can be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions can contain, for example, from about 0.1% by weight to about 99% by weight, e.g., from about 10-60% by weight, of the active material, depending on the method of administration. Where the compositions comprise dosage units, each unit will contain, for example, from about 1-1000 mg of the active ingredient. The dosage as employed for adult human treatment will range, for example, from about 1-3000 mg per day, for instance 1500 mg per day depending on the route and frequency of administration. Such a dosage corresponds to about 0.015-50 mg/kg per day. Suitably the dosage is, for example, from about 5-20 mg/kg per day.

Representative pharmaceutical formulations containing a compound of formula (I) are described below.

The present invention also provides a process for preparing a compound of the invention, e.g. a compound of formula (I) which process comprises reacting a compound of formula (V)

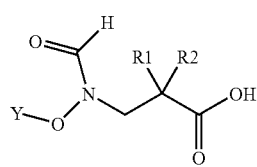
(V)

wherein $R_1$ and $R_2$ are as defined above and Y is a hydroxy protecting group, or a functional derivative thereof, with a compound of formula (VI)

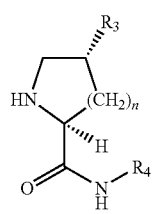
(VI)

wherein $R_3$ and $R_4$ are as defined above, and n is equal to 1, and where required, converting the resulting compounds obtained in free form into salt forms or vice versa.

Functional derivatives of compounds of formula (V) include e.g. acid chloride, acid anhydride or an activated ester.

Above reactions may be carried out according to methods known in the art or as disclosed in the Examples below. The reaction may conveniently be carried out in the presence of a base and then followed by hydrogenation, preferably in the presence of a hydrogenation catalyst. Suitable bases include e.g. Hunig base (i.e. diisopropylethylamine) and inorganic bases such as sodium bicarbonate. The hydrogenation catalyst, preferably a palladium catalyst, e.g. palladium on carbon or palladium black, may then be added to the resulting product, e.g. after concentration and stirred under a hydrogen atmosphere e.g. for about 16 to about 24 hours. The palladium catalyst may be added preferably from about 5 mol % to about 10 mol % of the concentrated product.

Compounds of formula (V), used as starting materials, may be prepared e.g. by reacting a compound of formula (VII)

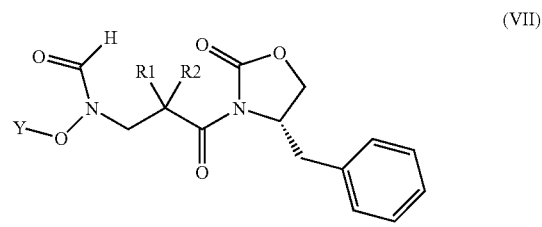
(VII)

wherein $R_1$, $R_2$, and Y are as defined above, e.g. under mild basic conditions e.g. as known in the art. Typically, this reaction may be carried out by dissolving the compound of formula (VII) e.g. in a mixture of an inert solvent, such as THF, DMF, toluene, dioxane or $CH_2Cl_2$, and water, and adding hydrogen peroxide and then an aqueous solution of the base in water to the cooled mixture. Examples of base include, e.g. sodium bicarbonate, lithium hydroxide, sodium hydroxide and the like. The base may be used preferably at from about 1.1 to about 1.5 equivalents to the compound of formula (VII).

Compounds of formula (VII) may be produced e.g. by reacting a compound of formula (VIII) wherein $R_1$, $R_2$, and Y are as defined above, with formic acid as known in the art. The reaction may typically be carried out, e.g. at 0° C., by adding a solution of acetic anhydride in formic acid to a solution of a compound of formula (VIII) in formic acid.

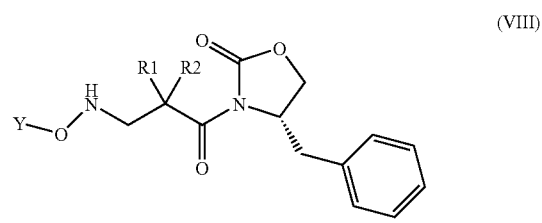
(VIII)

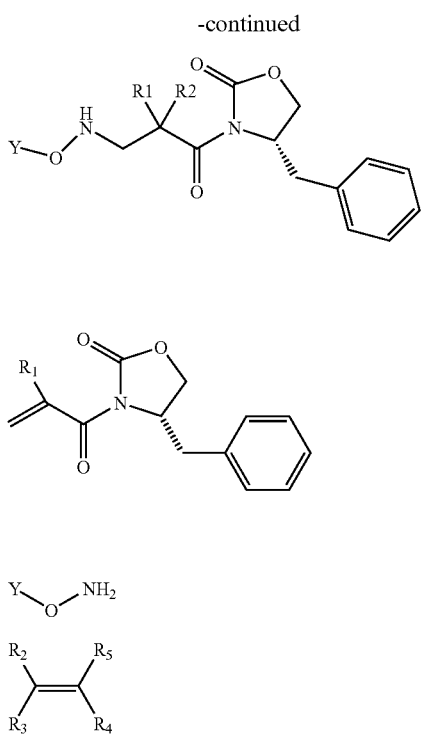

Compounds of formula (VIII) may be prepared e.g. by reacting a compound of formula (IX) wherein $R_1$, $R_2$, and Y are as defined above, with a solution of p-toluenesulfonic acid in an inert organic solvent, and a solution of $Na_2CO_3$, e.g. 1M, as known in the art.

Compounds of formula (IX) may be prepared e.g. by reacting a compound of formula (X) wherein $R_1$ is as defined above, with a hydroxy protected compound of formula (XI) wherein Y is aryl, alkyl, aralkyl or silyl, as known in the art.

The compound of formula (X) may be produced e.g. by reacting a compound of formula (XII) with pivaloyl chloride, wherein $R_4$ is as defined above, as known in the art.

Insofar as the production of starting materials is not particularly described, the compounds are known or may be prepared analogously to methods known in the art or as disclosed in the examples hereinafter.

All patents, patent applications and publications cited in this application are hereby incorporated by reference in their entirety for all purposes to the same extent as if each individual patent, patent application or publication were so individually denoted.

The following abbreviations are used:

AcOH, HOAc=acetic acid $Ac_2O$=acetic anhydride

BOC, Boc=t-butyloxycarbonyl

DCM=dichloromethane

DIEA=diisopropylethylamine

DMF=dimethylformamide

DMSO=dimethylsulfoxide

Et=ethyl

EtOAc=ethyl acetate

Fmoc, FMOC=9-fluorenylmethyloxycarbonyl

HATU=O-(7-aza-benzotriazol-1-yl)-N,N,N',N'-tetramethyluronium hexafluorophosphate MCPBA=meta-chloroperoxy-benzoic acid Me=methyl MeOH=methanol MMP=matrix metalloproteinase NVOM=nitroveratryloxymethyl ether p-TSA=p-toluenesulfonic acid RT=room temperature TFA=trifluoroacetic acid tBu=t-butyl THF=tetrahydrofuran THP=2-tetrahydropyranyl TsOH or p-TSA=toluenesulfonic acid General Synthetic Scheme Compounds of this invention can be made by the methods depicted in the reaction schemes shown below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1-15 (John Wiley and Sons, 1991); Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Preparation of Compounds of Formula (I)

Compounds of formula (I) can be prepared by methods well known in the art of organic chemistry. Representative synthetic procedures for preparing compounds of the present invention are illustrated and described in detail below. For example, compounds of formula (I) can be prepared as described in Schemes A-B below.

General Procedure A

Synthesis of 1-{2(R)-[(formylhydroxyamino)-methyl]-alkanoyl}-pyrrolidine-2(S)-carboxylic acid amide

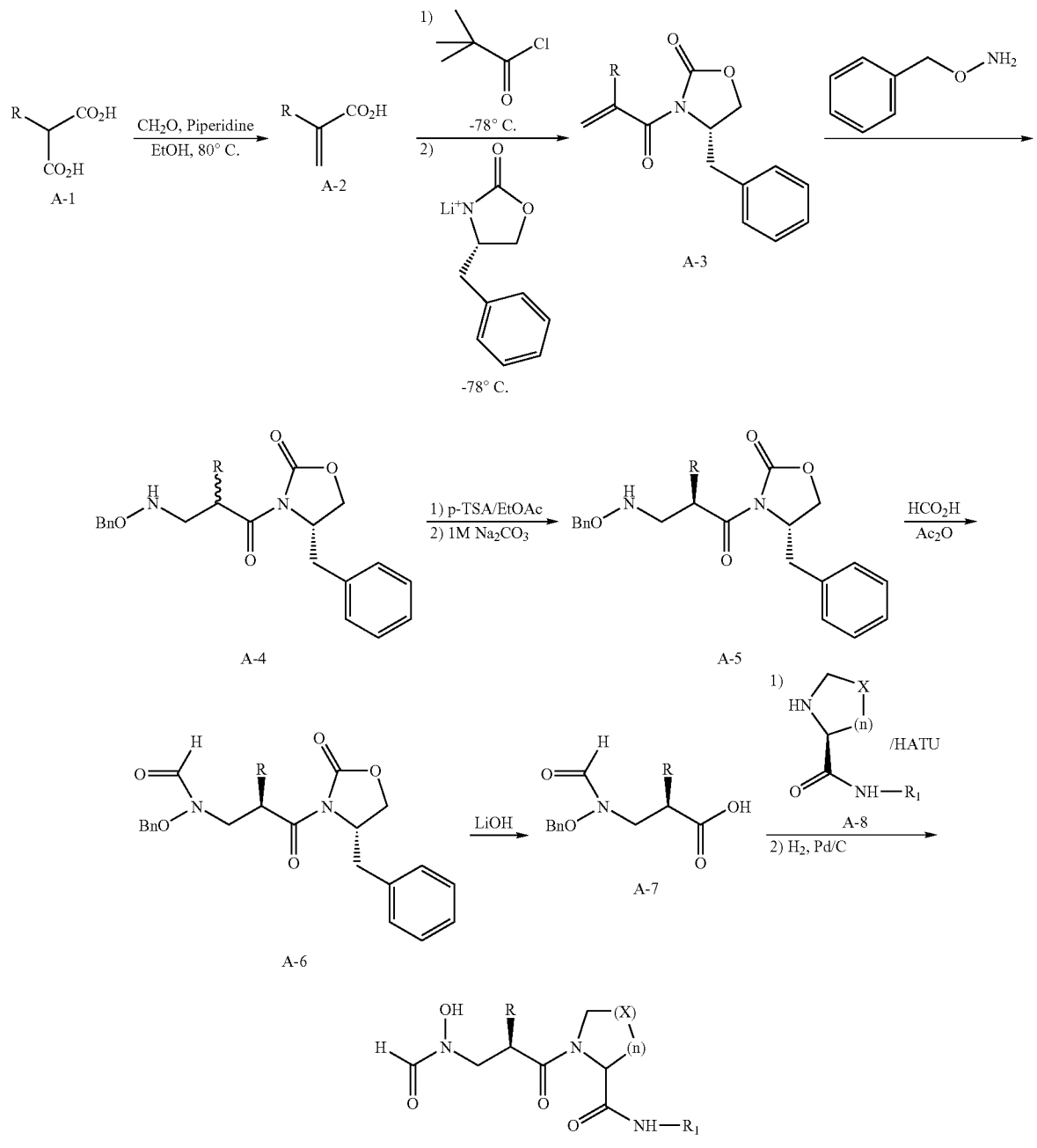

X = CH₂, S
n = 0, 1, 2

Step 1: 2-n-butyl acrylic acid (A-2)

To a solution of alkyl malonic acid A-1 (R=n-butyl (107.4 mmol) in ethanol (200 mL) is added piperidine (12.7 mL, 128.8 mmol, 1.2 equiv.) and 37% aqueous formaldehyde (40.0 mL, 536.9 mmol, 5 equiv.). The solution is heated to 80° C. during which time a precipitate appears, and then gradually redissolves over 1 hour. The reaction mixture is stirred at 80° C. overnight then cooled to room temperature (rt). The solvents are removed under reduced pressure, and the residue is dissolved in ethyl acetate, washed successively with 1 M HCl and brine, dried over anhyd Na₂SO₄, and filtered. The filtrate is concentrated to give the title compound A-2 as a clear oil.

Step 2: 4-benzyl-3-(2-butyl-acryloyl)-oxazolidin-2-one (A-3)

2-n-Butyl acrylic acid (9.90 g, 77.2 mmol, and 1 equiv.) is dissolved in dry THF (260 mL) and cooled to −78° C. under a blanket of nitrogen. Hunig's base (17.5 mL, 100.4 mmol, 1.3 equiv.) and pivaloyl chloride (9.5 mL, 77.2 mmol, 1 equiv.) are added at such a rate that the temperature remained below −60° C. The mixture is stirred at −78° C. for 30 minutes, warmed to rt for 2 hours, and finally cooled back to −78° C.

In a separate flask, (S)-(−)-4-benzyl-2-oxazolidinone (13.49 g, 77.24 mmol) is dissolved in dry THF (150 mL) and cooled to −78° C. under a blanket of nitrogen. n-Butyllithium (2.5 M solution in hexanes, 30.9 mL, 77.2 mmol, 1 equiv.) is added slowly at −78° C., and the mixture is stirred for 30 minutes at rt. The resulting anion is slowly transferred via a cannula into the original reaction vessel. The mixture is allowed to warm to rt and is stirred overnight at rt. The reaction is quenched with 1 M $KHCO_3$, and the solvents are removed under reduced pressure. The residue is partitioned between ethyl acetate and water. The organic layer is washed with brine, dried over anhydrous $Na_2SO_4$, filtered, and concentrated to give a yellow oil which is purified by flash chromatography (hexane:ethyl acetate=4:1) to yield the title compound A-3 as a white solid (15.0 g, 52.2 mmol, 68%).

Step 3: 4-benzyl-3-[2-(benzyloxyamino-methyl)-hexanoyl]-oxazolidin-2-one (p-toluenesulfonic acid salt)

Compound A-3 (8.25 g, 28.7 mmol) is mixed with O-benzylhydroxylamine (7.07 g, 57.4 mmol, 2 equiv.) and stirred for 40 hours at rt under nitrogen. The mixture is dissolved in ethyl acetate and p-toluenesulfonic acid (21.84 g, 114.8 mmol, and 4 equiv.) is added to precipitate excess O-benzylhydroxylamine as a white solid. The white solid is filtered off, and the filtrate is concentrated to give a crude yellow oil (HPLC analysis indicated a small trace of starting material). Charging the crude yellow oil with excess diethyl ether and cooling to 0° C. for 30 minutes gives a solid which is collected by filtration and dried in vacuo to afford the title compound as a white crystalline solid (single diastereomer).

Step 4: 4-benzyl-3-[2-(benzyloxyamino-methyl)-hexanoyl]-oxazolidin-2-one (A-5)

To a solution of p-TSA salt (22.9 g, 39.3 mmol) dissolved in ethyl acetate (400 mL), was added 1 M $Na_2CO_3$ (200 mL, 5 equiv.) and stirred at rt for 30 minutes. The layers were separated, and the aqueous layer extracted with ethyl acetate. The combined organic layers were dried over anhyd $Na_2SO_4$, filtered, and concentrated to give the title compound as a pale opaque oil (15.8 g, 38.6 mmol, 98%).

Step 5: N-[2-(4-benzyl-2-oxo-oxazolidine-3-carbonyl]-hexyl]-N-benzyloxy-formamide (A-6)

A solution of compound A-5 (5.38 g, 13.1 mmol, 1 equiv.) in formic acid (7.4 mL, 196.6 mmol, 15 equiv.) is cooled to 0° C. under a blanket of nitrogen. In a separate flask, formic acid (7.4 mL, 196.6 mmol, 15 equiv.) is cooled to 0° C. under a blanket of nitrogen, and acetic anhydride (2.47 mL, 26.2 mmol, 2 equiv.) is added dropwise. The solution is stirred at 0° C. for 15 minutes. The resulting mixed anhydride is slowly transferred via syringe into the original reaction vessel. The mixture is stirred at 0° C. for 1 hour, then at rt for 3 hours. The mixture is concentrated, taken up in dichloromethane, and washed successively with saturated $NaHCO_3$ and brine. The organic layer is dried over anhydrous $Na_2SO_4$, filtered, and concentrated to give an opaque oil which is purified by flash chromatography (hexane:ethyl acetate=2:1 then dichloromethane:acetone=9:1) to yield the title compound as a colorless oil.

Step 6: 2-[(benzyloxy-formyl-amino)-methyl]-hexanoic acid (A-7)

Compound A-6 (0.163 g, 0.372 mmol, 1 equiv.) is dissolved in THF (4.5 mL) and water (1.5 mL) and cooled to 0° C. Hydrogen peroxide (30% in water, 228 µL, 2.23 mmol, 6 equiv.) is added dropwise followed by the slow addition of a solution of lithium hydroxide (0.019 g, 0.446 mmol, 1.2 equiv.) in water (350 µL). The resulting mixture is stirred at 0° C. for 1.5 hours. The basic reaction mixture is quenched with Amberlite IR-120 resin ($H^+$) to pH 4-5 at 0° C. The resin is filtered off and rinsed with ethyl acetate. The mixture is concentrated to remove THF, and then taken up in ethyl acetate. The aqueous layer is separated, and the organic layer dried over anhydrous $Na_2SO_4$, filtered, and concentrated to give an opaque oil which was purified by flash chromatography (dichloromethane:acetone=4:1 then acetone: methanol=99:1) to yield the title compound A-7 as a colorless oil.

Step 7: 1-{2-[(benzyloxy-formyl-amino)-methyl]-hexanoyl}-pyrrolidine-2-carboxylic acid amide To a solution of compound A-7 (0.190 g, 0.680 mmol, 1 equiv.) in dry dioxane (4 mL) at rt under nitrogen is added successively Hunig's base (391 µL, 2.24 mmol, 3.3 equiv.), amine A-8 (0.748 mmol, 1.1 equiv.) and HATU (0.284 g, 0.748 mmol, 1.1 equiv.). The resulting mixture is stirred at rt for 22 hours. The mixture is partitioned between ethyl acetate and 10% citric acid. The organic layer is washed with brine and saturated $NaHCO_3$, dried over anhydrous $Na_2SO_4$, filtered, and concentrated. The residue is purified by flash chromatography (dichloromethane:acetone=3:1) to give the title compound as a colorless oil.

Step 2: 1{2-[(formyl-hydroxy-amino)-methyl]-hexanoyl}-pyrrolidine-2-carboxylic acid amide (A-9)

Pd—C (0.059 g, 0.1 equiv.) is added to a solution of above compound (0.550 mmol, 1 equiv.) in a 1:1 ethyl acetate/ethanol solution (12 mL) under a blanket of nitrogen. The mixture is stirred under hydrogen atmosphere for 36 hours. The catalyst is removed by filtration through a pad of Celite. The filtrate is concentrated, and the residue was purified by preparative TLC (dichloromethane:acetone=2:1) to give the title compound as an amorphous solid (0.121 g, 0.334 mmol, 61%).

General Procedure B

Synthesis of 1-{2(R)-[(formylhydroxyamino)-methyl]-alkanoyl}-pyrrolidine-2(S)-carboxylate ester

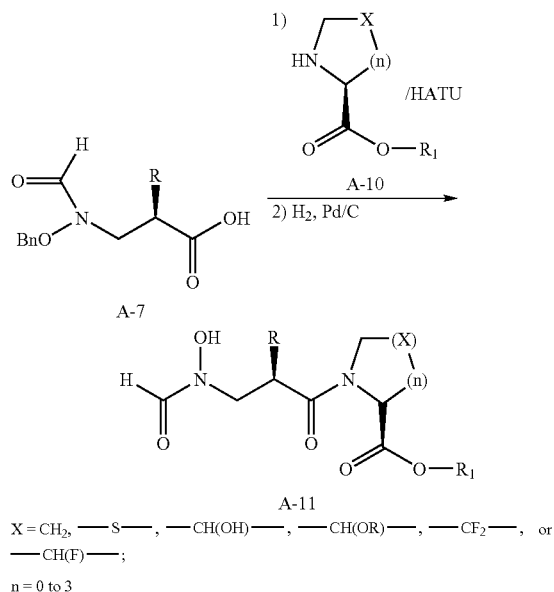

X = CH₂, —S—, —CH(OH)—, —CH(OR)—, —CF₂—, or —CH(F)—;

n = 0 to 3

Step 1: 1-{2-[(benzyloxy-formyl-amino)-methyl]-hexanoyl}-pyrrolidine-2-carboxylic acid ester To a solution of compound A-7 (0.680 mmol, 1 equiv.) in dry dioxane (4 mL) at rt under nitrogen is added successively Hunig's base (391 μL, 2.24 mmol, 3.3 equiv.), amine A-10 (0.748 mmol, 1.1 equiv.) and HATU (0.284 g, 0.748 mmol, 1.1 equiv.). Usual work-up and purification provides the title compound.

Step 2: 1{2-[(formyl-hydroxy-amino)-methyl]-hexanoyl}-pyrrolidine-2-carboxylic acid ester (A-11)

Pd—C (0.059 g, 0.1 equiv.) is added to a solution of above compound (0.550 mmol) in a 1:1 ethyl acetate/ethanol solution (12 mL) under a blanket of nitrogen. The mixture is stirred under hydrogen atmosphere for 36 hours. The catalyst is removed by filtration through a pad of Celite. The filtrate is concentrated, and the residue is purified by preparative TLC (dichloromethane:acetone=2:1) to give the title compound.

General Procedure C

Preparation of pyrrolidine-2-S-carboxylic acid pyridin-2-ylamide (A-8) (X=CH₂, n=1, R₁=2-pyridyl)

Step 1: 2-S-(pyridin-2-ylcarbamoyl)-pyrrolidine-1-carboxylic acid benzyl ester A-12

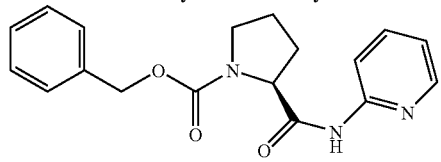

A solution of Z-prochloride (5.0 g, 18.7 mmol, 1 equiv.) in pyridine (40 mL) is cooled to 0° C. under a blanket of nitrogen. 2-aminopyridine (5.27 g, 56.0 mmol, 3 equiv.) in pyridine (10 mL) is added dropwise. The resulting mixture is stirred at rt for 4 hours, then concentrated. The residual oil is dissolved in ethyl acetate and washed successively with water, 10% citric acid, saturated NaHCO₃, and brine. The organic layer is dried over anhydrous Na₂SO₄, filtered, and concentrated to give the title compound (4.21 g, 13.0 mmol, 69%) as an opaque solid.

Step 2: Pyrrolidine-2-S-carboxylic acid (pyridin-2-yl) amide hydrobromic acid salt

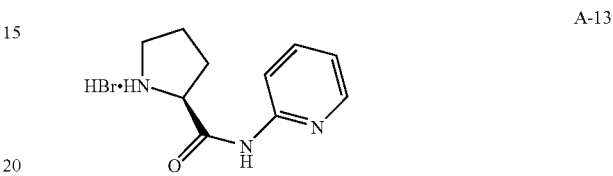

A solution of above compound (4.21 g, 13.0 mmol, 1 equiv.) in acetic acid (65 mL) at rt is treated with HBr (5.7 M, 33% in acetic acid, 110 mL, 649 mmol, 50 equiv.), and the mixture is stirred at rt for 2 hours. Charging the reaction mixture with excess diethyl ether and cooling to 0° C. for 30 minutes gives a solid which is collected by filtration and dried in vacuo to afford the title compound as a brownish powder.

General Procedure D

4-R-hydroxy-pyrrolidine-2-S-carboxylic acid (5-methyl-pyridine-2-yl)-amide

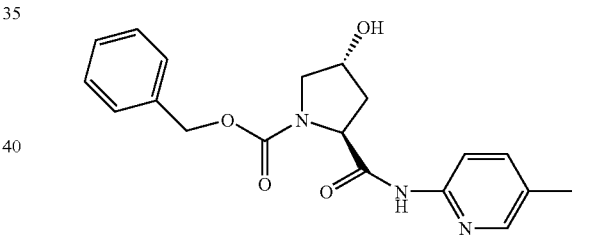

The coupling of O-tert butyl protected proline (1 mmol) with 5-picoline (1.5 mmol) in DMF (5 mL) under HATU (1.3 mmol) and N,N-diisopropylethyl amine (5 mmol) condition followed by removal of O-tert butyl with TFA-dichloroethane (1:1) provides the title compound in 85% yield.

General Procedure E

4-S-fluoro-pyrrolidine-2-S-carboxylic acid (5-methyl-pyridine-2-yl)-amide

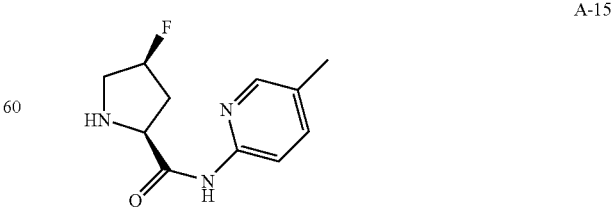

The above hydroxy compound (2 mmol) in methylenechloride (20 mL) is treated with N'N-diethylamino sulphur trifluoride (DAST; 4 mmol) at −70° C. Then, reaction mixture is allowed to stir at rt for 16 hours and washed with cold aq. sodium bicarbonate solution, dried and concentrated under reduced pressure. It is purified on silica gel column chromatography to give N-protected derivative which on treatment with HBr—AcOH provides an amino compound General Procedure F 4-S-hydroxy-pyrrolidine-1,2-dicarboxylic acid 1-tert-butyl ester-2-methyl ester

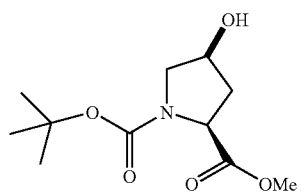

A-16

To a solution of trans-4-hydroxy compound (1 mmol), triphenyl phosphine (1.5 mmol) and benzoic acid (1.5 mmol) in THF (10 mL) is added N,N-diisopropyl-azo dicarboxylate (1.5 mmol) in THF (5 mL) dropwise at 0° C. It is allowed to stir at rt for 16 hours. The solvent is removed under reduced pressure and residue is dissolved in ether. It is ice cooled to precipitate phosphine oxide which is removed by filtration and filtrate is concentrated under reduced pressure. The crude material is treated with methanolic sodium methoxide for 2 hours at 0° C. to give title cis-hydroxy compound.

General Procedure G

4-R-fluoro-pyrrolidine-2-S-carboxylic acid (5-methyl-pyridine-2-yl)-amide

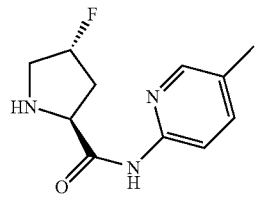

A-17

The fluorination of the above cis-hydroxy provides the trans-4-fluoro derivative which on saponification gives the corresponding acid. The amine is prepared from 4-R-fluoro-pyrrolidine-1-carboxylic acid tert-butyl ester and 5-methyl-pyridin-2-ylamine under HATU condition to give proline amide derivative which on treatment with 4 M HCl in dioxane provides the desired amine.

EXAMPLE 1

1-[2-Cyclopentylmethyl-3-(formyl-hydroxy-amino)-propionyl]-pyrrolidine-2-carboxylic acid (5-fluoro-1-oxy-pyridin-2-yl)-amide

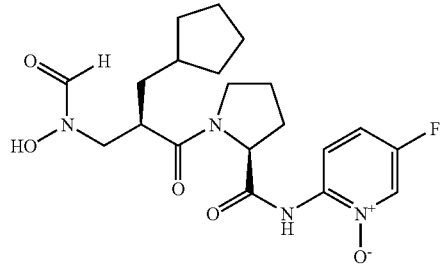

A-18

The title compound is prepared according to General Procedure A from 3-benzyloxy-formyl-amino)-2-cyclopentylmethyl-propionic acid A-7 (R=cyclopentylmethyl) and pyrrolidine-2-carboxylic acid pyridin-2-ylamide A-8 (X=CH$_2$, n=1, R$_1$=5-Fluoro 2-pyridyl).

2-Cyclopentylmethyl-3-[formyl-(tetrahydro-pyran-2-yloxy)-amino]-propionic acid

Is prepared from cyclopentylmethyl malonic acid as described below.

Bromomethyl-cyclopentane

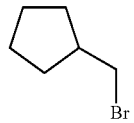

A-18a

A solution of cyclopentane methanol (48.5 g, 484 mmol), Et$_3$N (88.0 mL, 631 mmol), and anhydrous THF (1 L) is cooled to 4° C., and stirred under nitrogen. Methanesulfonyl chloride (45.0 mL, 581 mmol) is slowly added to the stirring solution, while maintaining 10° C. The mixture is stirred for an additional hour at 10° C., and LiBr (300.0 g, 3454 mmol) is slowly added (exothermic). The reaction mixture is stirred for an additional 16 hours at room temperature. Water is added to dissolve the salt, and the mixture is extracted with Et$_2$O. The Et$_2$O layers are combined, dried over Na$_2$SO$_4$, and is carefully concentrated (25° C. at 100 torr). The crude product is purified by vacuum distillation (35° C. at 1 torr, the desired compound is the first fraction to be collected). This gives bromomethyl-cyclopentane (31.4 g, 40% yield) as a colorless oil.

2-Cyclopentylmethyl-malonic acid

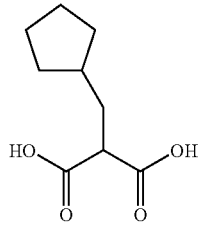

A-18b

A solution of diethyl malonate (36.91 g, 230.4 mmol), anhydrous methanol (400 mL), and NaOMe (25% in methanol, 49.79 g, 230.4 mmol) is stirred at reflux for one hour under nitrogen. Bromomethyl-cyclopentane (31.31 g, 192.0 mmol) is added to the mixture, and stirred for an additional 3 hours. A solution of NaOH (23.04 g, 576.0 mmol) in water (400 mL) is added, and the mixture is stirred for an additional 1 hour at reflux. The mixture is cooled, diluted with water, and extracted with ether. The ether layer is discarded, and the aqueous layer is acidified with 1N HCl to pH=1. The aqueous layer is extracted with EtOAc. The EtOAc layers are combined, dried over Na$_2$SO$_4$, and concentrated. This gives 2-cyclopentylmethyl-malonic acid (21.0 g, 59% yield) as a white solid.

2-Cyclopentylmethyl-acrylic acid

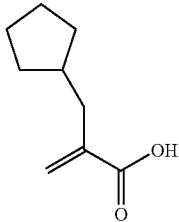

A-18c

A mixture of 2-cyclopentylmethyl-malonic acid (24.90 g, 133.7 mmol), piperidine (15.9 mL, 160.8 mmol), 37% aqueous formaldehyde (51.0 mL, 647.2 mmol), and EtOH (250 mL) is stirred at reflux for 16 hours. The reaction is quenched with 1N HCl to a pH=1, and the mixture is extracted with EtOAc. The EtOAc layers are combined, dried over $Na_2SO_4$, and concentrated. The crude product is purified by flash chromatography ($SiO_2$, 10% acetone in DCM), which gives 2-cyclopentylmethyl-acrylic acid (17.65 g, 86% yield) as an oil.

4-Benzyl-3-(2-cyclopentylmethyl-acryloyl)-oxazolidin-2-one

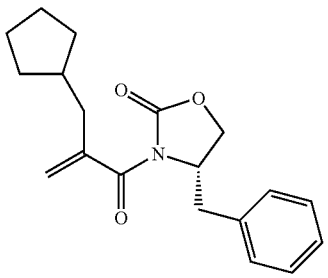

A-18d

2-Cyclopentylmethyl-acrylic acid (17.65 g, 114.5 mmol) is dissolved in anhydrous THF (200 mL) and cooled to −78° C. under nitrogen. N,N-Diisopropylethylamine (25.9 mL, 148.7 mmol) and trimethylacetyl chloride (14.1 mL, 114.5 mmol) are added consecutively at such a rate that the temperature remained below −60° C. and that gas evolution is controlled. The mixture is stirred at −78° C. for 30 minutes, stirred at room temperature for 2 hours, and cooled back down to −78° C.

In a separate flask, (S)-(−)-4-benzyl-2-oxazolidinone (20.30 g, 114.6 mmole) is dissolved in anhydrous THF (400 mL) and cooled to −78° C. under nitrogen. BuLi (2.5M, 45.8 mL, 114.5 mmole) is slowly added at −78° C., and the mixture is stirred for 30 minutes at room temperature. The resulting anion is slowly transferred via a cannula into the original reaction vessel. The mixture is allowed to warm to room temperature, and is stirred overnight at room temperature (16 hours). The reaction mixture is quenched with 1M $KHCO_3$, and is extracted with EtOAc. The organic layers are combined, washed with brine, dried over $Na_2SO_4$, and concentrated to give a yellow oil. The crude product is purified by flash chromatography ($SiO_2$, 20% EtOAc in hexane) to give 4-benzyl-3-(2-cyclopentylmethyl-acryloyl)-oxazolidin-2-one (22.9 g, 64%) of as an oil.

4-Benzyl-3-[2-cyclopentylmethyl-3-(tetrahydro-pyran-2-yloxyamino)-propionyl]-oxazolidin-2-one

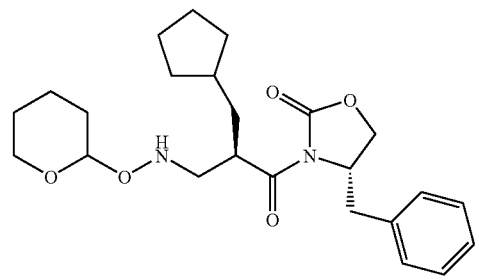

A-18e

4-Benzyl-3-(2-cyclopentylmethyl-acryloyl)-oxazolidin-2-one (22.90 g, 73.1 mmol) and O-(tetrahydro-2H-pyran-2-yl)-hydroxylamine (34.24 g, 292.3 mmol) is combined at stirred at 45° C. for 48 hours under nitrogen. The crude product is purified by flash chromatography ($SiO_2$, 0→30% EtOAc in hexane), which gives 4-benzyl-3-[2-cyclopentylmethyl-3-(tetrahydro-pyran-2-yloxyamino)-propionyl]-oxazolidin-2-one (21.65 g, 69% yield) as an oil.

N-[3-(4-Benzyl-2-oxo-oxazolidin-3-yl)-2-cyclopentylmethyl-3-oxo-propyl]-N-(tetrahydropyran-2-yloxy)-formamide

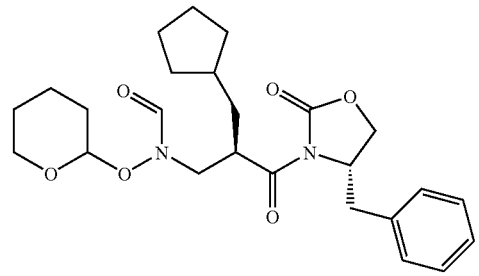

A-18f

A mixture of formic acid (45.0 mL, 1193 mmol) and acetic anhydride (90.0 mL, 952 mmol) is stirred at 50° C. for one hour under nitrogen. A second flask is charged with 4-benzyl-3-[2-cyclopentylmethyl-3-(tetrahydro-pyran-2-yloxyamino)-propionyl]-oxazolidin-2-one (21.62 g, 50.2 mmol), $Et_3N$ (170.0 mL, 1220 mmol), and anhydrous DCM (450 mL). This second mixture is cooled to 4° C. under nitrogen, and the mixed acid solution is slowly added to the second flask, while maintaining 10° C. The combined mixture is stirred for 30 minutes at 10° C., quenched with saturated, washed with aqueous $NaHCO_3$ solution, and extracted with DCM. The DCM layers are combined, dried over $Na_2SO_4$, and concentrated. The crude product is purified by flash chromatography ($SiO_2$, 50% EtOAc in hexane), which gives N-[3-(4-benzyl-2-oxo-oxazolidin-3-yl)-2-cyclopentylmethyl-3-oxo-propyl]-N-(tetrahydro-pyran-2-yloxy)-formamide (20.10 g, 87% yield) as an oil.

2-Cyclopentylmethyl-3-[formyl-(tetrahydro-pyran-2-yloxy)-amino]-propionic acid

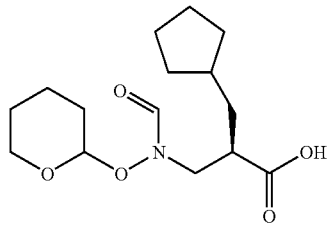

A-18g

N-[3-(4-Benzyl-2-oxo-oxazolidin-3-yl)-2-cyclopentylmethyl-3-oxo-propyl]-N-benzyloxy-formamide (compound A-G, where: R₁=cyclopenylmethyl, PG₁=benzyl)

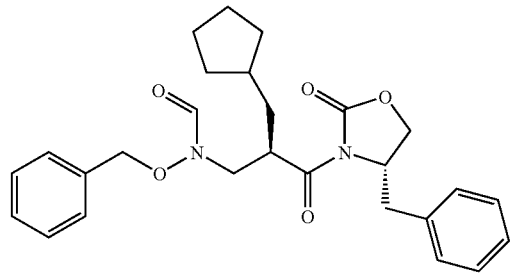

A-18i

N-[3-(4-Benzyl-2-oxo-oxazolidin-3-yl)-2-cyclopentylmethyl-3-oxo-propyl]-N-(tetrahydro-pyran-2-yloxy)-formamide (3.65 g, 7.96 mmol), THF (125 mL), and water (40 mL) is cooled to 4° C. To this mixture, is added 30% $H_2O_2$ (5.2 mL, 50.90 mmole) and LiOH monohydrate (0.40 g, 9.53 mmol), respectively. The reaction mixture is stirred for 1.5 hours. The mixture is slowly quenched with 0.5 M $Na_2SO_3$, while maintaining the temperature below 15° C. with an ice bath. The quenched mixture is stirred for an addition 30 minutes, concentrated in vacuo until the THF solvent is removed, and washed with EtOAc. The basic reaction mixture is acidified with Amberlite IR-120 resin (H+) to pH=4.5. Brine is added to the acidic solution, and the combined mixture is extracted with EtOAc. The organic layers from the acidic solution washing are combined, dried over $Na_2SO_4$, and concentrated in vacuo. This gave 2-cyclopentylmethyl-3-[formyl-(tetrahydro-pyran-2-yloxy)-amino]-propionic acid (1.20 g, 50% yield) as an oil.

3-(Benzyloxy-formyl-amino)-2-cyclopentylmethyl-propionic acid

Is prepared from 2-Cyclopentylmethyl-acrylic acid and O-benzyl hydroxamine as described for the synthesis of the corresponding O-THp protected building block.

[4-Benzyl-3-(3-benzyloxyamino-2-cyclopentylmethyl-propionyl)-oxazolidin-2-one

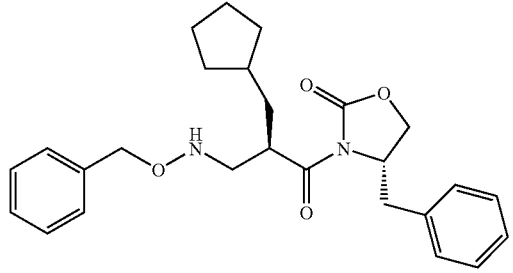

A-18h

3-(Benzyloxy-formyl-amino)-2-cyclopentylmethyl-propionic acid

A-18k

1-[3-Benzyloxy-formyl-amino)-2-cyclopentylmethyl-propionyl]-pyrrolidine-2-carboxylic acid (5-fluoro-1-oxy-pyridin-2-yl)-amide A-18l

EXAMPLE 2

4-Fluoro-1-{2-[(formyl-hydroxy-amino)-methyl]-hexanoyl}-pyrrolidine-2-carboxylic acid (5-fluoro-1-oxy-pyridin-2-yl)-amide

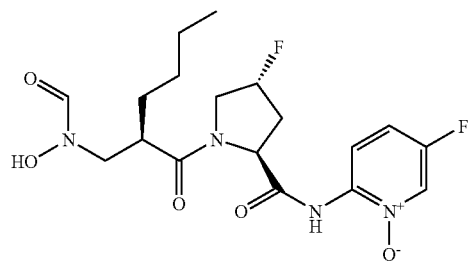

A-19

The title compound is prepared according to General Procedure A from 2-[(benzyloxy-formyl-amino)-methyl]-hexanoic acid A-7 (R=n-butyl) and pyrrolidine-2-carboxylic acid pyrrolidine-2-ylamide A-8 (X=CHF n=1, $R_1$=5-Fluoro 2-pyridyl).

4-trans-fluoro-pyrrolidine-2-carboxylic acid-[2-amino-5-fluoro-pyridin-2-yl]amide

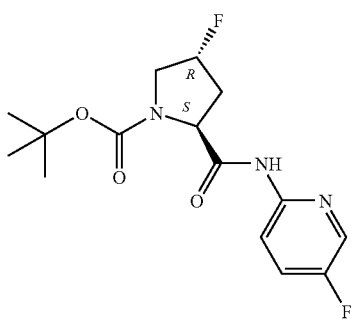

A-19a

To a DMF solution (15 mL) of Boc-L-Pro-4-F—OH (2.5 g, 10.73 mmol, 1 equiv) Hunig's base (Diisopropylethylamine, abbrev. DIEA) (6.73 mL, 38.61 mmol, 3.6 eq) is added and the mixture cooled to 0° C. This is followed by the addition of 2-Amino-5-fluoro pyridine (1.44 g, 12.87 mmol, 1.2 equiv), and HATU (4.89 g, 12.87 mmol, 1.2 equiv) at 0° C. The resulting mixture is stirred at room temperature for 16 h. The mixture is partitioned between excess ethyl acetate and 10% citric acid. The organic layer is washed with brine and sat. $NaHCO_3$, dried over anhydrous $Na_2SO_4$, filtered, and concentrated. The residue is purified by silica gel chromatography (Hexanes:Ethyl acetate=1:0-7:3) to give the title compound as a colorless syrup (2.5 g, 71%).

4-trans-fluoro-pyrrolidine-2-carboxylic acid-[2-amino-5-fluoro-pyridin-2-yl]amide (hydrochloric acid salt)

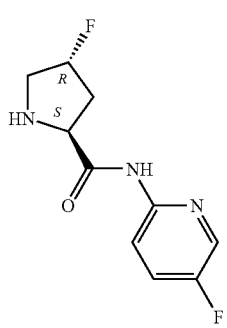

A-19b

The Boc-proline-4-fluoro-pyridine amide (1 g, 3.06 mmol, 1 equiv) is treated with 4N HCl/dioxane (30 mL, 120 mmol, 40 equiv) at room temperature and allowed to stir for 16 h. The mixture is concentrated, and the residue was coevaporated with toluene 2×, and concentrated to give a purplish pink solid (1 g).

1-{2-[(Benzyloxy-formyl-amino)-methyl]-hexanoyl}-4-trans-fluoro-pyrrolidine-2-carboxylic acid-(2-amino-5-fluoro-pyridin-2-yl)-amide

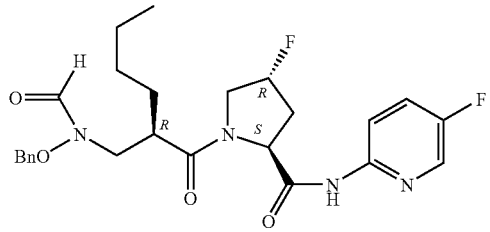

A-19c

To a DMF solution (10 mL) of trans-fluoro-proline-5-fluoro-aminopyridine amide HCl salt (644 mg, 2.15 mmol, 1.2 equiv), are successively added Hunig's base (2 mL, 10.8 mmol, 5 equiv), Versiacid VRI 172 (500 mg, 1.79 mmol, 1 equiv), and HATU (818 mg, 2.15 mmol, 1.2 equiv) at 0° C. The resulting mixture is stirred at room temperature for 16 h. The mixture is partitioned between excess ethyl acetate and 10% citric acid. The organic layer is washed with brine and sat. $NaHCO_3$, dried over anhydrous $Na_2SO_4$, filtered, and concentrate. The compound is purified by silica gel chromatography in DCM:Acetone (1:0-86:14) to give the title compound as a white powder (630 mg, 72%). ES-MS: calcd. for $C_{25}H_{30}F_2N_4O_5$ (504.53). found: 505.4 [M+H].

1-{2-[(Benzyloxy-formyl-amino)-methyl]-hexanoyl}-4-trans-fluoro-pyrrolidine-2-carboxylic acid-(2-amino-5-fluoro-pyridin-N-oxide-2-yl)-amide

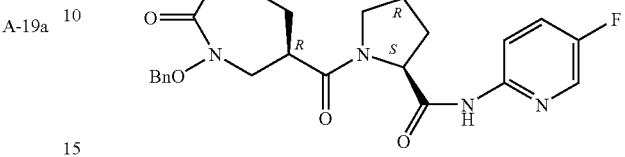

A-19d

To a DCM solution of the compound (1.25 g, 2.56 mmol, 1 eq), MCPBA (1.32 g, 7.68 mmom, 3 eq) was successfully added at 0° C. and the reaction was stirred for 16 h. The reaction mixture is partitioned between $NaHCO_3$ and the DCM layer. The organic layer is dried over $Na_2SO_4$ and concentrated. The residue is purified by silica gel chromatography using DCM:Acetone (1:0-9:1) to yield the title compound (1.2 g

EXAMPLE 3

1-{2-[(Formyl-hydroxy-amino)-methyl]-hexanoyl}-pyrrolidine-2-carboxylic acid pyrazin-2-ylamide

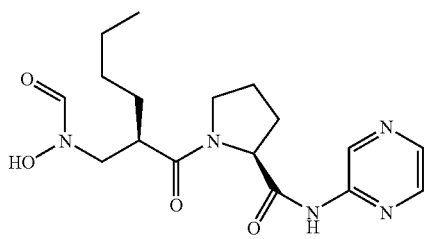

A-20

The title compound is prepared according to General Procedure A from 2-[(benzyloxy-formyl-amino)-methyl]-hexanoic acid A-7 (R=n-butyl) and pyrrolidine-2-carboxylic acid pyrazin-2-amide A-8 (X=CH$_2$, n=1, R$_1$=2-pyrazinyl).

EXAMPLE 4

1-{2-[(Formyl-hydroxy-amino)-methyl]-hexanoyl}-pyrrolidine-2-carboxylic acid pyridazin-3-ylamide

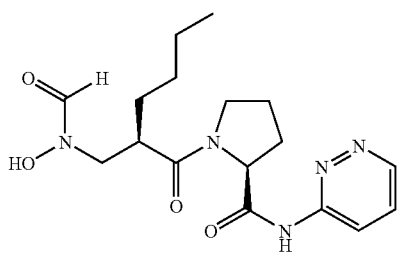

A-21

The title compound is prepared according to General Procedure A from 2-{[formyl-(tetrahydro-pyran-2-yloxy)-amino]-methyl}-hexanoic acid A-7 (R=n-butyl) and pyrrolidine-2-carboxylic acid pyridazin-3-amide A-8 (X=CH$_2$, n=1, R$_1$=3-pyridazinyl).

Step 1: Pyridazin-3-ylamine

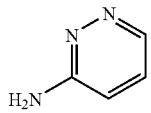

A-21a

To a solution of 6-chloro-2-amino-pyridiazine (4 g) and NaOH (powdered, 1.4 g) in ethanol (150 ml), 10% Pd/C (0.6 g) is added. The reaction mixture is stirred under Hydrogen atmosphere for 16 h. It is filtered through celite and the solvent was concentrated. The resulting residue is triturated with ether to provide the known amino compound.

Step 2: 2-(Pyridazin-3-ylcarbamoyl)-pyrrolidine-1-carboxylic acid tert-butyl ester

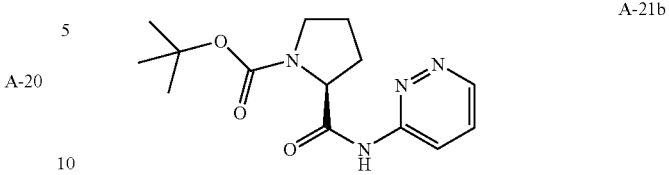

A-21b

To a solution of Boc-Pro-OH (1 equiv) in DCM at 0° C., Ghosez Reagent (1.1 equiv) is added and the reaction mixture was stirred at 0° C. for 1 h. To this the amine (1.1 equiv) in pyridine is added and the reaction mixture is stirred at room temperature for 16 h. It is then concentrated to remove all volatiles and redissolved in excess DCM. The organic layer is washed with 10% Citric acid, Brine and NaHCO$_3$, dried over Na2SO4 and concentrated. The resulting residue is purified by flash chromatography using 10-40% Ethyl acetate in hexanes to provide the title compound. HPLC: YMC-Pak Pro C18, S-3 □m, 120 A, 50×4.6 mm I.D. Column; gradient eluent 0%-90% MeCN over 8.5 min, 1.5 mL/min; Retention time=4.14 min.

ES-MS: calcd. for C$_{14}$H$_{20}$N$_4$O$_3$ (292). found 293 [M+H].

Step 2: Pyrrolidine-2-carboxylic acid pyridazin-3-ylamide

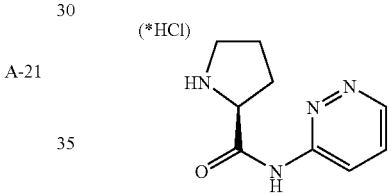

(*HCl)

HPLC: YMC-Pak Pro C18, S-3 □m, 120 A, 50×4.6 mm I.D. Column; gradient eluent 0%-90% MeCN over 8.5 min, 1.5 mL/min; Retention time=2.398 min.

ES-MS: calcd. for C$_9$H$_{12}$N$_4$O (192.1). found 193.2 [M+H].

Step 3: 1-(2-{[Formyl-(tetrahydro-pyran-2-yloxy)-amino]-methyl}-hexanoyl)-pyrrolidine-2-carboxylic acid pyridazin-3-ylamide

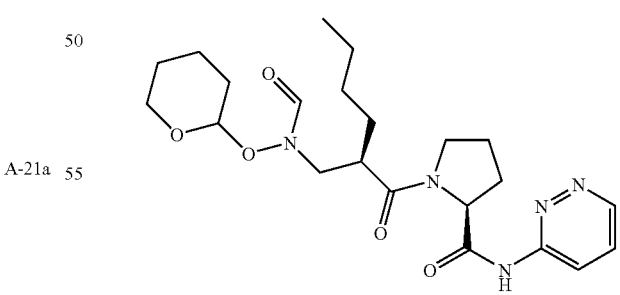

The title compound is prereprared under HATU condition as described in general procedure A.

HPLC: YMC-Pak Pro C18, S-3 □m, 120 A, 50×4.6 mm I.D. Column; gradient eluent 20%-90% MeCN over 8.5 min, 1.5 mL/min; Retention time=3.655 min ES-MS: calcd. for C$_{22}$H$_{33}$N$_5$O$_5$ (447). found 448 [M+H]. .

EXAMPLE 5

1-[2-Cyclopentylmethyl-3-(formyl-hydroxy-amino)-propionyl]-4-fluoro-pyrrolidine-2-carboxylic acid (5-fluoro-1-oxy-pyridin-2-yl)-amide

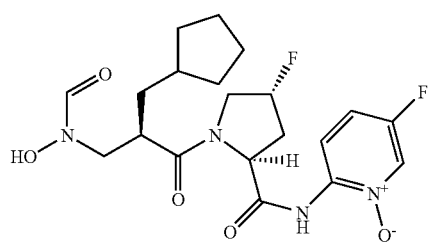

A-22

The title compound is prepared according to General Procedure A from 2-cyclopentylmethyl-3-[formyl-(tetrahydro-pyran-2-yloxy)-amino]-propionic acid and pyrrolidine-2-carboxylic acid pyridin-2-ylamide A-8 (X=CHF, n=1, $R_1$=5-Fluoro 2-pyridyl).

1-{2-Cyclopentylmethyl-3-[formyl-(tetrahydro-pyran-2-yloxy)-amino]-propionyl}-4-fluoro-pyrrolidine-2-carboxylic acid (5-fluoro-1-oxy-pyridin-2-yl)-amide

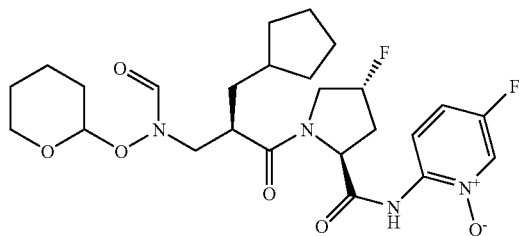

A-22a

EXAMPLE 6

1-[2-Cyclobutylmethyl-3-(formyl-hydroxy-amino)-propionyl]-pyrrolidine-2-carboxylic acid pyridazin-3-ylamide

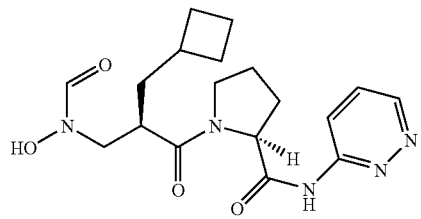

A-23

The title compound is prepared according to General Procedure A from 2-cyclobutylmethyl-3-[formyl-(tetrahydro-pyran-2-yloxy)-amino]-propionic acid A-7 (R=cyclobutylmethyl) and pyrrolidine-2-carboxylic acid pyridazin-2-amide A-8 (X=$CH_2$, n=1, $R_1$=3-pyridazinyl).

EXAMPLE 7

1-[2-Cyclobutylmethyl-3-(formyl-hydroxy-amino)-propionyl]-pyrrolidine-2-carboxylic acid pyrazin-2-ylamide

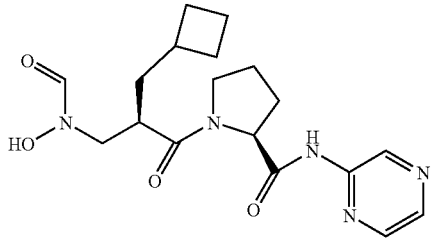

A-24

The title compound is prepared according to General Procedure A from 2-cyclobutylmethyl-3-[formyl-(tetrahydro-pyran-2-yloxy)-amino]-propionic acid A-7 (R=cyclobutylmethyl) and pyrrolidine-2-carboxylic acid pyrazin-2-amide A-8 (X=$CH_2$, n=1, $R_1$=2-pyrazinyl).

EXAMPLE 8

1-[2-Cyclopentylmethyl-3-(formyl-hydroxy-amino)-propionyl]-pyrrolidine-2-carboxylic acid pyrazin-2-ylamide

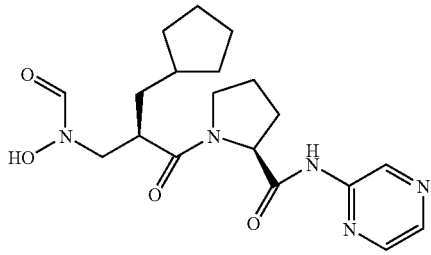

A-25

The title compound is prepared according to General Procedure A from 2-cyclopentylmethyl-3-[formyl-(tetrahydro-pyran-2-yloxy)-amino]-propionic acid A-7 (R=cyclopentylmethyl) and pyrrolidine-2-carboxylic acid pyrazin-2-amide A-8 (X=$CH_2$, n=1, $R_1$=2-pyrazinyl).

EXAMPLE 9

4-Fluoro-1-{2-[(formyl-hydroxy-amino)-methyl]-hexanoyl}-pyrrolidine-2-carboxylic acid pyrazin-2-ylamide

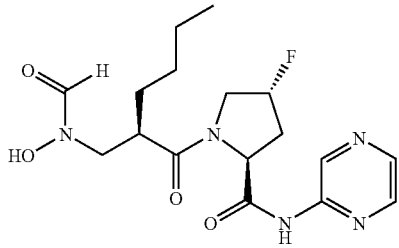

A-26

The title compound is prepared according to General Procedure A from 2-[(benzyloxy-formyl-amino)-methyl]-hexanoic acid A-7 (R=n-butyl) and pyrrolidine-2-carboxylic acid pyrazin-2-amide A-8 (X=CHF, n=1, $R_1$=2-pyrazinyl).

EXAMPLE 10

1-[2-Cyclopentylmethyl-3-(formyl-hydroxy-amino)-propionyl]-4-fluoro-pyrrolidine-2-carboxylic acid pyrazin-2-ylamide

A-27

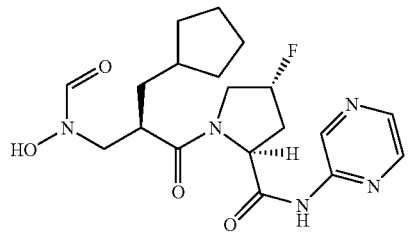

The title compound is prepared according to General Procedure A from 2-cyclopentylmethyl-3-(formyl-hydroxy-amino)-propionic acid A-7 (R=cyclopentyl methyl) and pyrrolidine-2-carboxylic acid pyrazin-2-amide A-8 (X=CHF, n=1, $R_1$=2-pyrazinyl).

EXAMPLE 11

1-[2-Cyclobutylmethyl-3-(formyl-hydroxy-amino)-propionyl]-4-fluoro-pyrrolidine-2-carboxylic acid pyrazin-2-ylamide

A-28

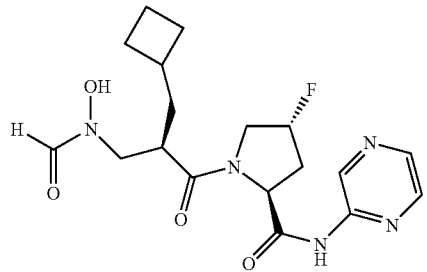

The title compound is prepared according to General Procedure A from 2-cyclobutylmethyl-3-[formyl-(tetrahydro-pyran-2-yloxy)-amino]-propionic acid A-7 (R=cyclobutyl methyl) and pyrrolidine-2-carboxylic acid pyrazin-2-amide A-8 (X=CHF, n=1, $R_1$=2-pyrazinyl).

2-Cyclobutylmethyl-3-[formyl-(tetrahydro-pyran-2-yloxy)-amino]-propionic acid is prepared from 2-cyclobutylmethyl malonic acid as described for the synthesis of the corresponding cyclopentylmethyl derivative in Example 1.

2-Cyclobutylmethyl-malonic acid

A-28a

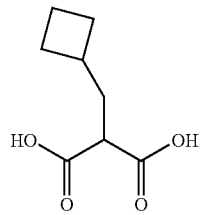

The title compound is prepared from (bromomethyl)cyclobutane

2-Cyclobutylmethyl-acrylic acid

A-28b

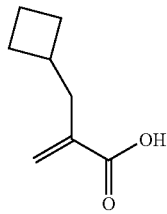

4-Benzyl-3-(2-cyclobutylmethyl-acryloyl)-oxazolidin-2-one

A-28c

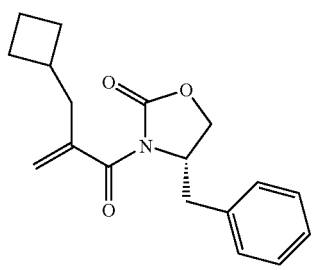

4-Benzyl-3-[2-cyclobutylmethyl-3-(tetrahydro-pyran-2-yloxyamino)-propionyl]-oxazolidin-2-one A-28d

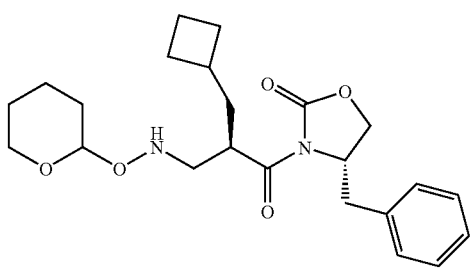

N-[3-(4-Benzyl-2-oxo-oxazolidin-3-yl)-2-cyclobutylmethyl-3-oxo-propyl]-N-(tetrahydropyran-2-yloxy)-formamide A-28e

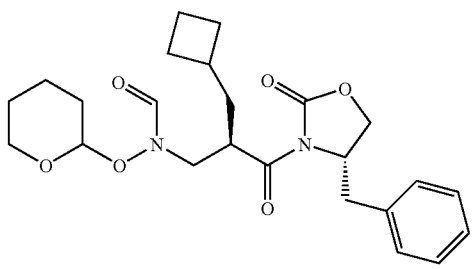

2-Cyclobutylmethyl-3-[formyl-(tetrahydro-pyran-2
yloxy)-amino]-propionic acid

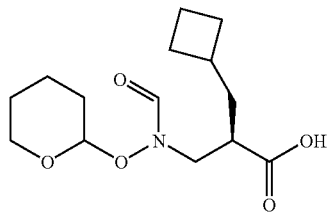

A-28f

1-{2-Cyclobutylmethyl-3-[formyl-(tetrahydro-pyran-
2-yloxy)-amino]-propionyl}-4-fluoro-pyrrolidine-2-
carboxylic acid pyrazin-2-ylamide A-28g

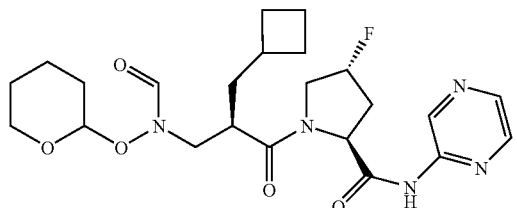

EXAMPLE 12

1-[2-Cyclobutylmethyl-3-(formyl-hydroxy-amino)-
propionyl]-4-fluoro-pyrrolidine-2-carboxylic acid
pyrimidin-4-ylamide

A-29

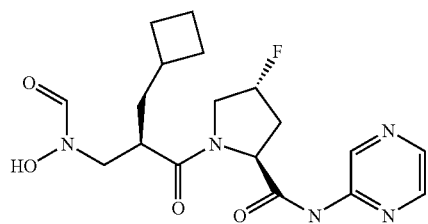

The title compound is prepared according to General Procedure A from 2-cyclobutylmethyl-3-[formyl-(tetrahydro-pyran-2-yloxy)-amino]-propionic acid A-7 (R=cyclobutyl methyl) and pyrrolidine-2-carboxylic acid pyrimidin-4-amide A-8 (X=CHF, n=1, R₁=2-pyrimidinyl).

EXAMPLE 13

1-[2-Cyclobutylmethyl-3-(formyl-hydroxy-amino)-
propionyl]-4-fluoro-pyrrolidine-2-carboxylic acid
pyridazin-3-ylamide

A-30

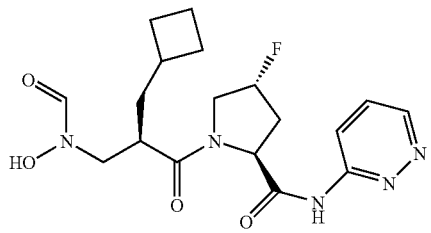

The title compound is prepared according to General Procedure A from 2-cyclobutylmethyl-3-[formyl-(tetrahydro-pyran-2-yloxy)-amino]-propionic acid A-7 (R=cyclobutyl methyl) and pyrrolidine-2-carboxylic acid pyridazin-3-amide A-8 (X=CHF, n=1, R₁=3-pyridazinyl).

(2S,4R)-tert-butyl 4-fluoro-2-(pyridazin-3-ylcarbamoyl)pyrrolidine-1-carboxylate A-30a

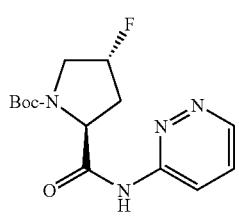

To a solution of Boc-Pro(F)—OH (5 g, 21.46 mmol, 1 equiv) in DCM at 0° C., Ghosez Reagent (3.1 ml, 23.61 mmol, 1.1 equiv) is added and the reaction mixture was stirred at 0° C. for 1 h. To this the amine (2.65 g, 27.9 mmol, 1.3 equiv) in Pyridine is added at 0° C. and the reaction mixture is stirred at room temperature for 16 h. It is then concentrated to remove all volatiles and redissolved in excess DCM. The organic layer is washed with 10% Citric acid, NaCl(sat) and NaHCO₃(sat), dried over Na₂SO4 and concentrated. The resulting residue is purified by flash chromatography using 10-15% Acetone in Dichloromethane to provide the title compound.

(2S,4R)-4-fluoro-N-(pyridazin-3-yl)pyrrolidine-2-
carboxamide

A-30b

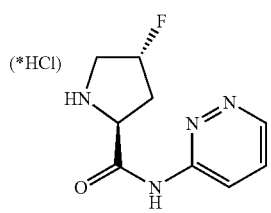

The Boc-protected amide is taken into 4M HCl/Dioxane and the reaction is stirred at room temperature for 5 h. The solvent are removed under reduced pressure and the residue is triturated with ether to give the title compounds (2S,4R)-1-((2R)-3-cyclobutyl-2-((N-(tetrahydro-2H-pyran-2-yloxy)formamido)methyl)propanoyl)-4-fluoro-N-(pyridazin-3-yl)pyrrolidine-2-carboxamide

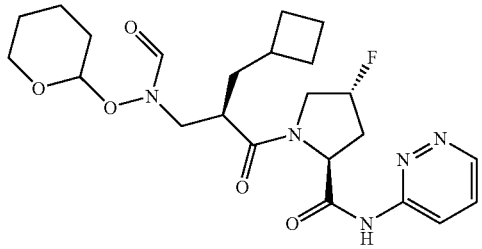

A-30c

To a cold DMF solution (15 mL) of the Versiacid, (500 mg, 1.77 mmol, 1 equiv), DIEA (1.7 ml, 9.72 mmol, 5.5 equiv), Amine.HCl salt (550 mg, 1.943 mmol, 1.1 equiv) and HATU (739 mg, 1.943 mmol, 1.2 equiv) are added. The resulting reaction mixture is stirred for 16 h at room temperature. The mixture is partitioned between excess ethyl acetate and 10% citric acid. The organic layer is washed with sat. NaCl and sat. NaHCO$_3$, dried over anhydrous Na$_2$SO$_4$, filtered, and concentrated. The residue is purified by silica gel chromatography using 10-25% Acetone in DCM to give the title compound (53%).

EXAMPLE 14

1-[2-Cyclobutylmethyl-3-(formyl-hydroxy-amino)-propionyl]-4-fluoro-pyrrolidine-2-carboxylic acid (2-oxy-pyridazin-3-yl)-amide

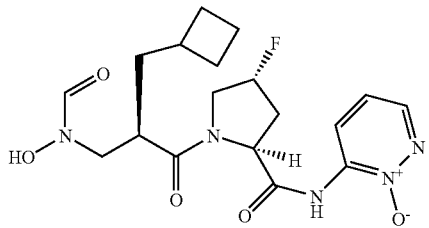

A-31

The title compound is prepared according to General Procedure A from 2-Cyclobutylmethyl-3-[formyl-(tetrahydro-pyran-2-yloxy)-amino]-propionic acid A-7 (R=cyclobutyl methyl) and pyrrolidine-2-carboxylic acid pyridazin-1-oxo-3-amide A-8 (X=CHF, n=1, R$_1$=3-pyridazinyl N-oxide).

6-((2S,4R)-1-(tert-butoxycarbonyl)-4-fluoropyrrolidine-2-carboxamido)pyridazine 1-oxide

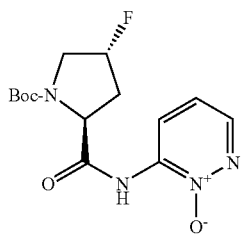

A-31c

To a solution of Boc-Pro(F)—OH (2.047 g, 8.154 mmol, 1 equiv) in DCM at 0° C., Ghosez Reagent (1.2 ml, 8.97 mmol, 1.1 equiv) is added and the reaction mixture is stirred at 0° C. for 1 h. To this the amine (1.27 g, 11.42 mmol, 1.4 equiv) in Pyridine is added at 0° C. and the reaction mixture is stirred at room temperature for 16 h. It is then concentrated to remove all volatiles and the residue is dissolved in excess DCM. The organic layer is washed with 10% Citric acid, NaCl (sat) and NaHCO$_3$ (sat), dried over Na$_2$SO$_4$ and concentrated. The resulting residue is purified by flash chromatography using 2-15% Acetone in Dichloromethane to provide the title compound (61%).

6-((2S,4R)-4-fluoropyrrolidine-2-carboxamido)pyridazine 1-oxide

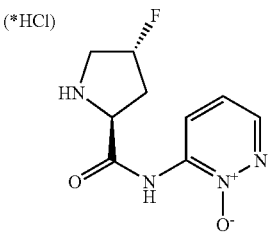

A-31d

The Boc-protected amide is taken into 4M HCl/Dioxane and the reaction is stirred at room temperature for 5 h. All volatiles are removed and the residue is triturated with ether to give the title compounds.

6-((2S,4R)-1-((2R)-3-cyclobutyl-2-((N-(tetrahydro-2H-pyran-2 yloxy)formamido)methyl)propanoyl)-4-fluoropyrrolidine-2-carboxamido)pyridazine 1-oxide

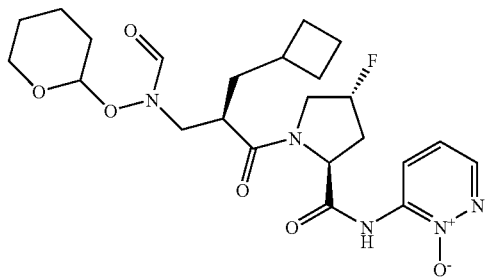

A-31e

To a cold DMF solution (20 mL) of the Versiacid, (571 mg, 2 mmol, 1 equiv), DIEA (2.51 ml, 14.4 mmol, 6 equiv), Amine.HCl salt (718 mg, 2.4 mmol, 1.2 equiv) and HATU (913 mg, 2.4 mmol, 1.2 equiv) are added. The resulting reaction mixture is stirred for 16 h at room temperature. The mixture is partitioned between excess ethyl acetate and 10% citric acid. The organic layer is washed with sat. NaCl and sat. NaHCO$_3$, dried over anhydrous Na$_2$SO$_4$, filtered, and concentrated. The residue is purified by silica gel chromatography using 10-20% Acetone in DCM and then using 2-8% methanol in DCM to give the title compound (44%). 1H NMR (DMSO-d$_6$):

EXAMPLE 15

1-[2-Cyclopentylmethyl-3-(formyl-hydroxy-amino)-propionyl]-4-fluoro-pyrrolidine-2-carboxylic acid pyridazin-3-ylamide

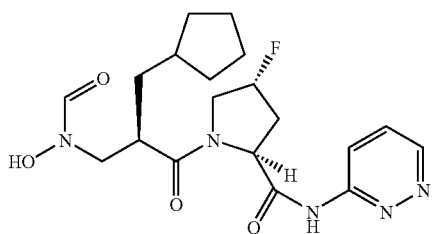

A-32

The title compound is prepared according to General Procedure A from 2-Cyclopentylmethyl-3-[formyl-(tetrahydro-pyran-2-yloxy)-amino]-propionyl acid A-7 (R=cyclopentyl methyl) and pyrrolidine-2-carboxylic acid pyridazin-2-amide A-8 (X=CHF, n=1, R₁=3-pyridazinyl).

(2S,4R)-1-((2R)-3-cyclopentyl-2-((N-(tetrahydro-2H-pyran-2-yloxy)formamido)methyl)propanoyl)-4-fluoro-N-(pyridazin-3-yl)pyrrolidine-2-carboxamide

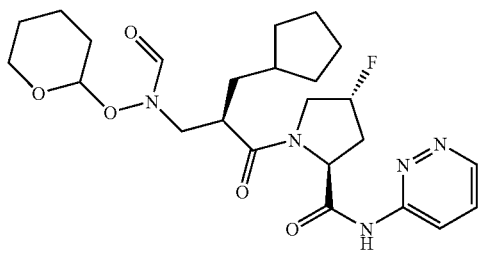

A-32b

EXAMPLE 16

1-[2-Cyclopentylmethyl-3-(formyl-hydroxy-amino)-propionyl]-4-fluoro-pyrrolidine-2-carboxylic acid (2-oxy-pyridazin-3-yl)-amide

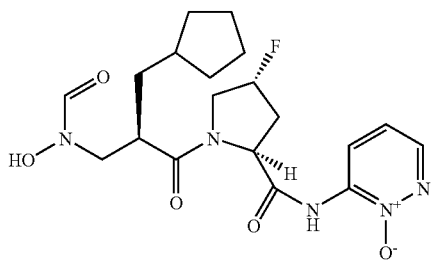

A-33

The title compound is prepared according to General Procedure A from 2-cyclopentylmethyl-3-[formyl-(tetrahydro-pyran-2-yloxy)-amino]-propionyl acid A-7 (R=cyclopentyl methyl) and pyrrolidine-2-carboxylic acid pyridazin-2-amide A-8 (X=CHF, n=1, R₁=3-pyridazinyl N-oxide).

6-aminopyridazine 1-oxide

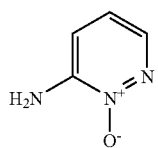

A-33a

To a solution of 6-Aminopyridazine in acetone is added a solution of MCPBA (1 equiv.) in acetone in one portion. The reaction mixture is allowed to stir at room temperature for 1 hour. The solvent is removed and ether is added to the residue. The solid is filtered and dried to yield the title compound. This is used as such in the next step.

6-((2S,4R)-1-(tert-butoxycarbonyl)-4-fluoropyrrolidine-2-carboxamido)pyridazine 1-oxide

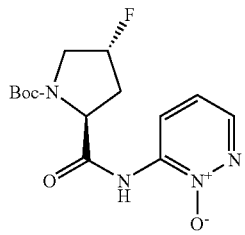

A-33b

To a solution of Boc-Pro(F)—OH (2.047 g, 8.154 mmol, 1 equiv) in DCM at 0° C., Ghosez Reagent (1.2 ml, 8.97 mmol, 1.1 equiv) is added and the reaction mixture is stirred at 0° C. for 1 h. To this the amine (1.27 g, 11.42 mmol, 1.4 equiv) in Pyridine is added at 0° C. and the reaction mixture is stirred at room temperature for 16 h. It is then concentrated to remove all volatiles and the residue is dissolved in excess DCM. The organic layer is washed with 10% Citric acid, NaCl(sat) and NaHCO₃(sat), dried over Na₂SO₄ and concentrated. The resulting residue is purified by flash chromatography using 2-15% Acetone in Dichloromethane to provide the title compound (61%).

6-((2S,4R)-4-fluoropyrrolidine-2-carboxamido)pyridazine 1-oxide

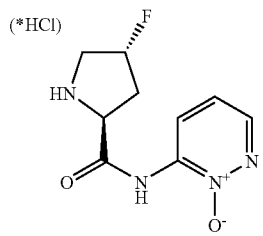

A-33c

The Boc-protected amide was taken into 4M HCl/Dioxane and the reaction was stirred at room temperature for 5 h. All volatiles were removed and the residue was triturated with ether to give the title compounds.

6-((2S,4R)-1-((2R)-3-cyclopentyl-2-((N-(tetrahydro-2H-pyran-2-yloxy)formamido)methyl)propanoyl)-4-fluoropyrrolidine-2-carboxamido)pyridazine 1-oxide A-33d

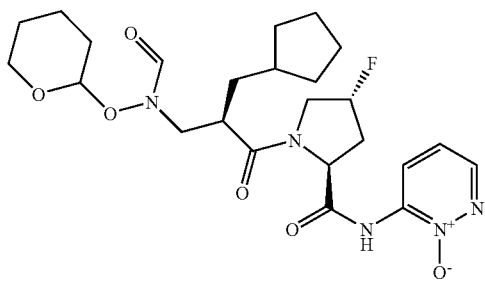

EXAMPLE 17

1-[2-Cyclohexylmethyl-3-(formyl-hydroxy-amino)-propionyl]-4-fluoro-pyrrolidine-2-carboxylic acid pyridazin-3-ylamide

A-34

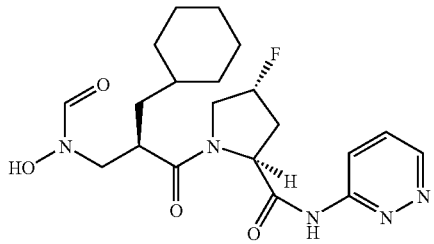

The title compound is prepared according to General Procedure A from 2-Cyclohexylmethyl-3-[formyl-(tetrahydro-pyran-2-yloxy)-amino]-propionyl acid A-7 (R=cyclohexyl methyl) and pyrrolidine-2-carboxylic acid pyridazin-3-amide A-8 (X=CHF, n=1, $R_1$=3-pyridazinyl).

2-Cyclohexylmethyl-3-(formyl-hydroxy-amino)-propionic acid building block is prepared from 2-cyclohexylmethylmalonic acid as described for the synthesis of the corresponding cyclohexylmethylmalonic acid in Example 1.

2-Cyclohexylmethyl-malonic acid

A-34a

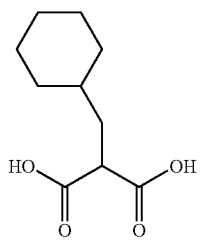

The title compound is prepared from (bromomethyl)cyclohexane.

2-Cyclohexylmethyl-acrylic acid

A-34b

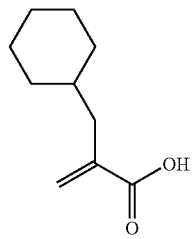

4-Benzyl-3-(2-cyclohexylmethyl-acryloyl)-oxazolidin-2-one

A-34c

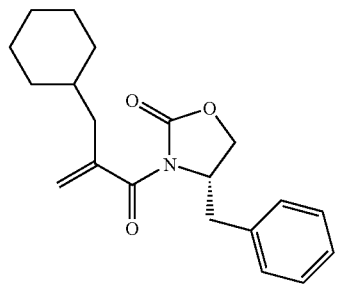

4-Benzyl-3-[2-cyclohexylmethyl-3-(tetrahydro-pyran-2-yloxyamino)-propionyl]-oxazolidin-2-one)

A-34d

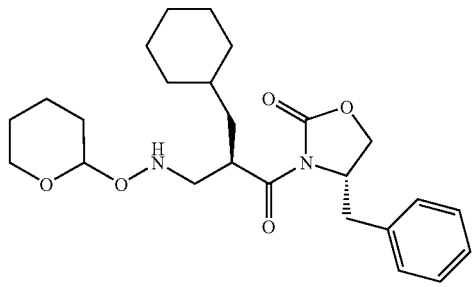

N-[3-(4-Benzyl-2-oxo-oxazolidin-3-yl)-2-cyclohexylmethyl-3-oxo-propyl]-N-(tetrahydropyran-2-yloxy)-formamide A-34e

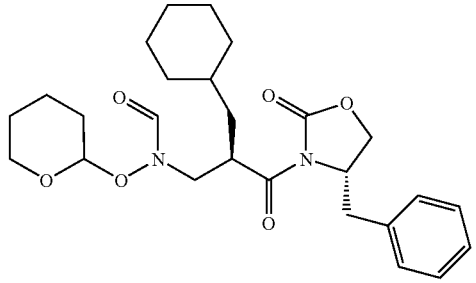

EXAMPLE 18

1-{4-Cyclopropyl-2-[(formyl-hydroxy-amino)-methyl]-butyryl}-4-fluoro-pyrrolidine-2-carboxylic acid pyrazin-2-ylamide

A-35

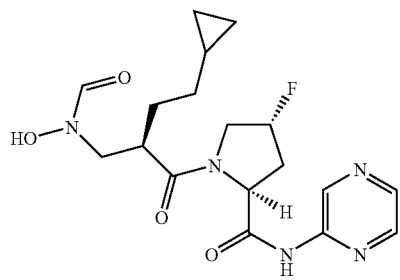

The title compound is prepared according to General Procedure A from 2-cyclopropylethyl-3-[formyl-(tetrahydro-pyran-2-yloxy)-amino]-propionic acid A-7 (R=cyclopropyl ethyl) and pyrrolidine-2-carboxylic acid pyrazin-2-amide A-8 (X=CHF, n=1, $R_1$=2-pyrazinyl).

2-Cyclopropylethyl-3-(formyl-hydroxy-amino)-propionic acid building block is prepared from 2-cyclopropylethylmalonic acid as described for the synthesis of the corresponding cyclopentylmethylmethyl malonic acid in Example 1.

(Bromoethyl)cyclopropane

A-35a

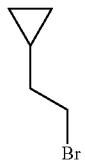

The title compound is prepared from 2-cyclopropylethanol.

2-Cyclopropylethyl-malonic acid

A-35b

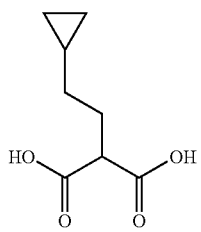

2-Cyclopropylethyl-acrylic acid

A-35c

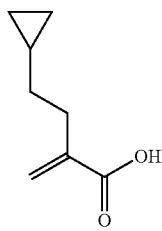

4-Benzyl-3-(2-cyclopropylethyl-acryloyl)-oxazolidin-2-one

A-35d

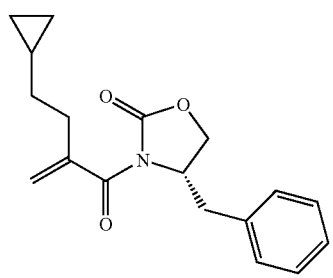

4-Benzyl-3-[2-cyclopropylethyl-3-(tetrahydro-pyran-2-yloxyamino)-propionyl]-oxazolidin-2-one A-35e

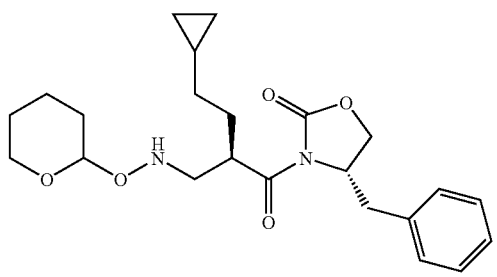

N-[3-(4-Benzyl-2-oxo-oxazolidin-3-yl)-2-cyclopropylethyl-3-oxo-propyl]-N-(tetrahydropyran-2-yloxy)-formamide A-35f

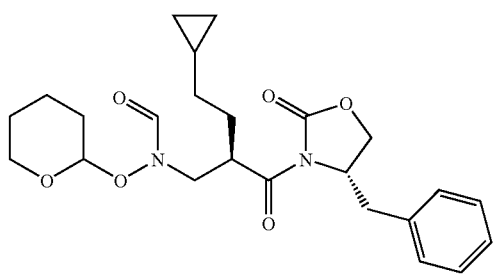

2-Cyclopropylethyl-3-[formyl-(tetrahydro-pyran-2-yloxy)-amino]-propionic acid

A-35g

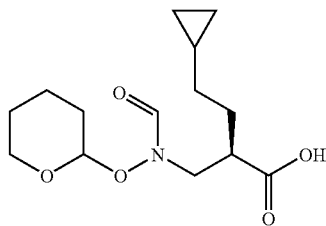

1-{2-Cyclopropylethyl-3-[formyl-(tetrahydro-pyran-2-yloxy)-amino]-propionyl}-4-fluoro-pyrrolidine-2-carboxylic acid pyrazin-2-ylamide A-35h

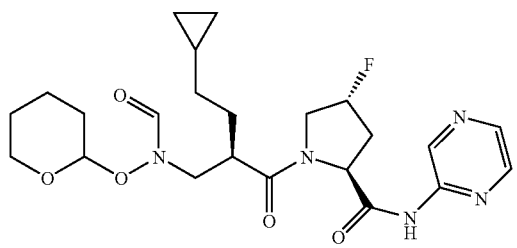

EXAMPLE 19

Inhibition of Peptide Deformylase Activity

A PDF/FDH coupled assay (Lazennec et al., Anal. Biochem., Vol. 224, pp. 180-182 (1997)) is used. In this coupled assay, the formate released by PDF from its substrate fMAS is oxidized by the coupling enzyme FDH, reducing one molecule of $NAD^+$ to NADH, which causes an increase in absorption at 340 nM. All assays are carried out at room temperature in a buffer of 50 mM HEPES, pH 7.2, 10 mM NaCl, 0.2 mg/mL BSA, in half-area 96-well microtiter plates (Corning). The reaction is initiated by adding a mixture of 0.5 Unit/mL FDH, 1 mM $NAD^+$, and fMAS at the desired concentration. To determine $IC_{50}$ (the concentration needed to inhibit 50% of enzyme activity) values, PDF is pre-incubated for 10 minutes with varying concentrations of the inhibitor, and the deformylation reaction is initiated by the addition of reaction mixture containing 4 mM fMAS. The initial reaction velocity, y, is measured as the initial rate of absorption increase at 340 nM using a SpectraMax plate reader (Molecular Devices, Sunnyvale, Calif.). The inhibitor concentration [In] at which 50% of the enzyme activity is inhibited, $IC_{50}$, is calculated using the following formula:

$$y=y_o/(1+[\text{In}]/IC_{50})$$

where $y_o$ is the reaction velocity in the absence of inhibitor. Solving this equation for $IC_{50}$ at the [In] when $y=y_o/2$ yields $IC_{50}$. The $IC_{50}$ is calculated based on a nonlinear least-square regression fit using a commercial software package (Deltapoint, Inc., Chicago, Ill.).

Using this assay, the $IC_{50}$ of various compounds are determined. The $IC_{50}$ for the various compounds is determined against deformylase enzyme containing nickel and zinc as the metal ion. The $IC_{50}$ values of preferred compounds of formula (I) determined for the zinc-containing deformylase range from about 0.001 µM to about 0.2 µM. The $IC_{50}$ values of preferred compounds of formula (I) determined for the nickel-containing deformylase range from about 0.005 µM to about 3 µM.

EXAMPLE 20

Assay for Testing Antimicrobial Activity

Minimum inhibitory concentrations (MICs) are determined using the microdilution method in 96-well format plates. Compounds are suspended in DMSO at 5 or 10 mg/mL and stored at 4° C. until used. They are diluted in Mueller-Hinton Broth (MHB) or Trypticase Soy Broth (TSB) and used for MIC determination. The range of concentrations tested is 64-0.0625 µg/mL final concentration using a two-fold dilution system.

The inoculum is prepared from cells grown on Trypticase Soy Agar (TSA) and incubated overnight at 35° C., 5-10 colonies are used to inoculate MHB or TSB broths, and the culture is incubated overnight at 35° C. The overnight culture is diluted 1:10, incubated for 1 hour at 35° C., diluted to the appropriate inoculum size and applied to the wells containing broth and test compound. Inoculum sizes are $2\times10^4$ CFU/mL.

Plates are incubated at 35° C. for 48 hours and MIC are recorded after 18 hours of incubation for bacteria. MIC is defined as the lowest concentration of compound that does not produce visible growth after incubation.

Minimum inhibitory concentration for various preferred compounds of formula (I) ranges from about 0.25 µg/mL to about 32 µg/mL against *H. influenza* (four strains), from about 0.001 µg/mL to greater than 8 µg/mL against *S. aureus* (four strains), from about 0.016 µg/mL to about 16 µg/mL against *S. pneumonia* (four strains), and from about 0.008 µg/mL to about 16 µg/mL against *M. catarrhalis*. The deformylase enzyme is obtained from *E. coli*.

The following are representative pharmaceutical formulations containing a compound of formula (I).

EXAMPLE 21

Tablet Formulation

The following ingredients are mixed intimately and pressed into single scored tablets:

| Quantity per Ingredient | Tablet (mg) |
| --- | --- |
| Compound of this invention | 400 |
| Cornstarch | 50 |
| Croscarmellose sodium | 25 |
| Lactose | 120 |
| Magnesium stearate | 5 |

EXAMPLE 22

Capsule Formulation

The following ingredients are mixed intimately and loaded into a hard-shell gelatin capsule:

| Quantity per | Ingredient Capsule (mg) |
| --- | --- |
| Compound of this invention | 200 |
| Lactose, spray -- dried | 148 |
| Magnesium stearate | 2 |

EXAMPLE 23

Suspension Formulation

The following ingredients are mixed to form a suspension for oral administration:

| Ingredient | Amount |
| --- | --- |
| Compound of this invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.0 g |
| Sorbitol (70% solution) | 13.00 g |
| Veegum K (Vanderbilt Co.) | 1.0 g |
| Flavoring | 0.035 mL |
| Colorings | 0.5 mg |
| Distilled water | q.s. to 100 mL |

EXAMPLE 24

Injectable Formulation

The following ingredients are mixed to form an injectable formulation:

| Ingredient | Amount |
| --- | --- |
| Compound of this invention | 0.2-20 mg |
| Sodium acetate buffer solution, 0.4M | 20 mL |
| HCl (1N) or NaOH (1N) | q.s. to suitable pH |
| Water (distilled, sterile) | q.s. to 20 mL |

EXAMPLE 25

Suppository Formulation

A suppository of total weight 2.5 g is prepared by mixing the compound of the invention with Witepsol® H-5 (triglycerides of saturated vegetable fatty acid; Riches-Nelson, Inc., New York), and has the following composition:

| Compound of the invention | 500 mg |
| --- | --- |
| Witepsol ® H-15 | Balance |

The invention claimed is:

1. A compound of formula (I)

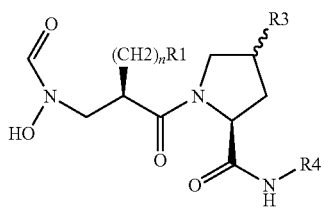

(I)

wherein R1 is hydrogen, alkyl, heteroalkyl, heterocycloalkyl, aryl, heteroaryl, or cycloalkyl;
R3 is hydrogen, halogen, or alkoxy;
R4 is a heteroaryl of formula (II.2)

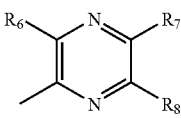

(II.2)

wherein
R6, R7 and R8 are hydrogen; or
R6 and R8 are hydrogen and R7 is alkyl, substituted alkyl or phenyl; or
R6 and R7 are hydrogen and R8 is halogen, alkyl or substituted alkyl; or
R7 and R8 are hydrogen and R6 is hydroxyl; and
n is 0 to 3 and
wherein one or more of the nitrogens of the pyrazinyl ring is optionally oxidized
or a salt thereof or a prodrug thereof.

2. A compound according to claim 1 wherein R3 is selected from fluorine, chlorine or iodine.

3. A compound according to claim 1 wherein R1 is cycloalkyl.

4. A compound according to claim 1 wherein R4 is a heteroaryl of formula (II.2)

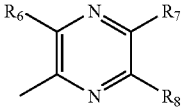

(II.2)

wherein R6, R7 and R8 are hydrogen, a salt thereof or a prodrug thereof.

5. A compound according to claim 1 wherein R1 is selected from cyclohexyl, cyclopentyl, cyclobutyl or cyclopropyl.

6. A compound according to claim 1 wherein R1 is an n-butyl.

7. A compound according to claim 5 wherein R4 is 2-pyrazine.

8. A compound according to claim 6 wherein R4 is 2-pyrazine.

9. A compound according to claim 5 wherein R3 is fluorine.

10. A compound according to claim 6 wherein R3 is fluorine.

11. A compound according to claim 1 wherein R4 is a heteroaryl of formula (II.2)

(II.2)

wherein
R6 and R8 are hydrogen and R7 is alkyl, substituted alkyl or phenyl; or
R6 and R7 are hydrogen and R8 is halogen, alkyl or substituted alkyl; or
R7 and R8 are hydrogen and R6 is hydroxyl;
a salt thereof or a prodrug thereof.

12. A compound according to claim 1, wherein the compound of formula (I) is 1-[2-cyclopentylmethyl-3-(formyl-hydroxy-amino)-propionyl]-4-fluoro-pyrrolidine-2-carboxylic acid pyrazin-2-ylamide or 1-[2-cyclobutylmethyl-3-(formyl-hydroxy-amino)-propionyl]-4-fluoro-pyrrolidine-2-carboxylic acid pyrazin-2-ylamide.

13. A compound according to claim 1, wherein the compound of formula (I) is 1-[2-cyclopentylmethyl-3-(formyl-hydroxy-amino)-propionyl]-4-fluoro-pyrrolidine-2-carboxylic acid pyrazin-2-ylamide.

* * * * *